US006682761B2

(12) United States Patent
Pace et al.

(10) Patent No.: US 6,682,761 B2
(45) Date of Patent: Jan. 27, 2004

(54) WATER-INSOLUBLE DRUG PARTICLE PROCESS

(75) Inventors: Gary W. Pace, Raleigh, NC (US); Awadesh K. Mishra, Montreal (CA)

(73) Assignee: RTP Pharma, Inc., Durham, NC (US)

( * ) Notice: Subject to any disclaimer, the term of this patent is extended or adjusted under 35 U.S.C. 154(b) by 8 days.

(21) Appl. No.: 09/838,540

(22) Filed: Apr. 20, 2001

(65) Prior Publication Data

US 2002/0012704 A1 Jan. 31, 2002

Related U.S. Application Data

(60) Provisional application No. 60/198,579, filed on Apr. 20, 2000.

(51) Int. Cl.⁷ .............................. A61K 9/14; B29B 9/00
(52) U.S. Cl. ........................... 424/489; 264/5; 424/400
(58) Field of Search ................... 424/449, 489; 264/5, 16, 13

(56) References Cited

U.S. PATENT DOCUMENTS

| | | |
|---|---|---|
| 2,803,582 A | 8/1957 | Cherney |
| 3,137,631 A | 6/1964 | Soloway |
| 3,216,897 A | 11/1965 | Krantz |
| 3,274,063 A | 9/1966 | Nieper et al. |
| 3,594,476 A | 7/1971 | Merrill |
| 3,715,432 A | 2/1973 | Merrill |
| 3,755,557 A | 8/1973 | Jacobs |
| 3,794,476 A | 2/1974 | Michalik et al. |
| 3,937,668 A | 2/1976 | Zolle |
| 3,960,757 A | 6/1976 | Morishita et al. |
| 3,965,255 A | 6/1976 | Bloch et al. |
| 4,016,100 A | 4/1977 | Suzuki et al. |
| 4,053,585 A | 10/1977 | Allison et al. |
| 4,056,635 A | 11/1977 | Glen et al. |
| 4,073,943 A | 2/1978 | Wretlind et al. |
| 4,078,052 A | 3/1978 | Papahadjopoulos |
| 4,089,801 A | 5/1978 | Schneider |
| 4,102,806 A | 7/1978 | Kondo et al. |
| 4,107,288 A | 8/1978 | Oppenheim et al. |
| 4,133,874 A | 1/1979 | Miller et al. |
| 4,145,410 A | 3/1979 | Sears |
| 4,147,767 A | 4/1979 | Yapel, Jr. |
| 4,186,183 A | 1/1980 | Steck et al. |
| 4,219,548 A | 8/1980 | Reller |
| 4,235,871 A | 11/1980 | Papahadjopoulos et al. |
| 4,241,046 A | 12/1980 | Papahadjopoulos et al. |
| 4,271,196 A | 6/1981 | Schmidt |
| 4,280,996 A | 7/1981 | Okamoto et al. |
| 4,298,594 A | 11/1981 | Sears et al. |
| 4,302,459 A | 11/1981 | Steck et al. |
| 4,308,166 A | 12/1981 | Marchetti et al. |
| 4,309,404 A | * 1/1982 | De Neale et al. ............. 424/21 |
| 4,309,421 A | 1/1982 | Ghyczy et al. |
| 4,316,884 A | 2/1982 | Alam et al. |
| 4,320,121 A | 3/1982 | Sears |
| 4,325,871 A | 4/1982 | Sasaki et al. |
| 4,328,222 A | 5/1982 | Schmidt |
| 4,329,332 A | 5/1982 | Couvreur et al. |
| 4,331,654 A | 5/1982 | Morris |
| 4,332,795 A | 6/1982 | Ghyczy et al. |
| 4,332,796 A | 6/1982 | Los |
| 4,340,594 A | 7/1982 | Mizushima et al. |
| 4,345,588 A | 8/1982 | Widder et al. |
| 4,351,831 A | 9/1982 | Growdon et al. |
| 4,356,167 A | 10/1982 | Kelly |
| 4,369,182 A | 1/1983 | Ghyczy et al. |
| 4,378,354 A | 3/1983 | Ghyczy et al. |
| 4,394,372 A | 7/1983 | Taylor |

(List continued on next page.)

FOREIGN PATENT DOCUMENTS

| | | |
|---|---|---|
| DE | 2 513 797 | 10/1975 |
| DE | 2 938 807 | 11/1980 |
| EP | 0 052 322 | 5/1982 |
| EP | 0 272 091 | 6/1988 |
| EP | 33 532 | 8/1989 |
| EP | 0 418 153 | 3/1991 |
| EP | 0 456 670 | 11/1991 |
| EP | 0 456 764 | 11/1991 |

(List continued on next page.)

OTHER PUBLICATIONS

"Phospholiponr® 100H", Technical Data, American Lecthin Co., Oxford, CT.
"Phospholiponr® 90H", Technical Data, American Lecthin Co., Oxford, CT.
Ross et al., "Aqueous Solutions of Surface–Active Solutes", *Collodial Systems and Interfaces*, © 1988, pp. 148–151.
Sande et al., "Antimicrobial Agents: Antifungal and Antiviral Agents", pp. 1219–1222.
Bittman, Robert, "Sterol–Polyene Antibiotic Complexation: Probe of Membrane Structure,"*Lipids,* 1978, vol. 13, No. 10, pp. 686–691.

(List continued on next page.)

*Primary Examiner*—Thurman K. Page
*Assistant Examiner*—Micah-Paul Young
(74) *Attorney, Agent, or Firm*—Edwards & Angell LLP

(57) ABSTRACT

This invention relates to process for the preparation of small particles containing a poorly water soluble drug comprising (a) mixing at high shear an admixture of a poorly water soluble drug and one or more than one surface active substance in an aqueous carrier in the absence of an organic solvent within a first temperature range at or above the melting point of the poorly water soluble drug to form a heated suspension containing the drug, then (b) homogenizing said heated suspension in a first pressure range and within said first temperature range to form a heated homogenate containing the drug, then (c) cooling said heated homogenate to a second temperature range below the melting temperature of the poorly water soluble drug to form a transiently stable cooled homogenate containing the drug, then (d) applying a particle stabilizing energetic process to said cooled homogenate within a second temperature range below the melting point of the drug and in a second pressure range to form a cooled dispersion of stabilized small particles containing the drug, and then (e) optionally drying the cooled dispersion to form dried small particles containing the poorly water soluble drug.

54 Claims, No Drawings

U.S. PATENT DOCUMENTS

| | | | |
|---|---|---|---|
| 4,397,846 A | 8/1983 | Weiner et al. | |
| 4,411,894 A | 10/1983 | Schrank et al. | |
| 4,421,747 A | 12/1983 | Ghyczy et al. | |
| 4,427,649 A | 1/1984 | Dingle et al. | |
| 4,448,765 A | 5/1984 | Ash et al. | |
| 4,483,847 A | 11/1984 | Augart | |
| 4,485,054 A | 11/1984 | Mezei et al. | |
| 4,492,720 A | 1/1985 | Mosier | |
| 4,515,736 A | 5/1985 | Deamer | |
| 4,529,561 A | 7/1985 | Hunt et al. | |
| 4,532,089 A | 7/1985 | MacDonald | |
| 4,610,868 A | 9/1986 | Fountain et al. | |
| 4,613,505 A | 9/1986 | Mizushima et al. | |
| 4,622,219 A | 11/1986 | Haynes | |
| 4,675,236 A | 6/1987 | Ohkawara et al. | |
| 4,687,762 A | 8/1987 | Fukushima et al. | |
| 4,725,442 A | 2/1988 | Haynes | |
| 4,756,910 A | 7/1988 | Yagi et al. | |
| 4,761,288 A | 8/1988 | Mezei | |
| 4,762,720 A | 8/1988 | Jizomoto | |
| 4,766,046 A | 8/1988 | Abra et al. | |
| 4,776,991 A | 10/1988 | Farmer et al. | |
| 4,800,079 A | 1/1989 | Boyer | |
| 4,801,455 A | 1/1989 | List et al. | |
| 4,803,070 A | 2/1989 | Cantrell et al. | |
| 4,806,350 A | 2/1989 | Gerber | |
| 4,806,352 A | 2/1989 | Cantrell | |
| 4,826,687 A | 5/1989 | Nerome et al. | |
| 4,839,111 A | 6/1989 | Huang | |
| 4,880,634 A | 11/1989 | Speiser | |
| 4,895,726 A | 1/1990 | Curtet et al. | |
| 4,961,890 A | 10/1990 | Boyer | |
| 4,973,465 A | 11/1990 | Baurain et al. | |
| 5,030,453 A | 7/1991 | Lenk et al. | |
| 5,091,187 A | 2/1992 | Haynes | |
| 5,091,188 A | 2/1992 | Haynes | |
| 5,098,606 A | * 3/1992 | Nakajima et al. | 252/358 |
| 5,100,591 A | 3/1992 | Leclef et al. | |
| 5,145,684 A | 9/1992 | Liversidge et al. | |
| 5,154,930 A | * 10/1992 | Poescu et al. | 424/489 |
| 5,246,707 A | 9/1993 | Haynes | |
| 5,272,137 A | 12/1993 | Blase et al. | |
| 5,302,401 A | 4/1994 | Liversidge et al. | |
| 5,320,906 A | 6/1994 | Eley et al. | |
| 5,336,507 A | 8/1994 | Na et al. | |
| 5,470,583 A | 11/1995 | Na et al. | |
| 5,545,628 A | 8/1996 | Deboeck et al. | |
| RE35,338 E | 9/1996 | Haynes | |
| 5,637,625 A | 6/1997 | Haynes | |
| 5,700,471 A | * 12/1997 | End et al. | 424/400 |
| 5,785,976 A | 7/1998 | Westesen et al. | |
| 5,827,536 A | 10/1998 | Laruelle | |
| 5,880,148 A | 3/1999 | Edgar et al. | |
| 5,922,355 A | 7/1999 | Parikh et al. | |

FOREIGN PATENT DOCUMENTS

| | | | |
|---|---|---|---|
| EP | 0 499 299 | 8/1992 | |
| EP | 724 877 | 8/1996 | |
| EP | 0 807 431 A2 | * 11/1997 | A61K/9/14 |
| EP | 757 911 | 12/1997 | |
| EP | 904 781 | 3/1999 | |
| GB | 2046094 | 9/1986 | |
| JP | 56167616 | 5/1980 | |
| JP | 55141407 | 11/1980 | |
| JP | 60208910 | 11/1980 | |
| JP | 63233915 | 10/1985 | |
| JP | 63502117 | 8/1987 | |
| JP | 1502590 | 7/1989 | |
| WO | WO 8500011 | 1/1985 | |
| WO | WO 8704592 | 8/1987 | |
| WO | WO 8804924 | 7/1988 | |
| WO | WO 9104011 | 4/1991 | |
| WO | WO 99/04761 | 2/1999 | |
| WO | WO 9904761 | 2/1999 | |
| WO | WO 9939700 | 8/1999 | |
| WO | WO 00/30616 | * 6/2000 | A61K/9/14 |

OTHER PUBLICATIONS

Mishra et al., "Scientifically Speaking: Novel Injectable Formulations of Water–Insoluble Drugs", *Controlled Release Newsletter*, Jun. 2000, vol. 17, Issue 2, pp. 21–30.

Bangham et al., "Diffusion of Univalent Ions Across the Lamellae of Swollen Phospholipids", *J. Mol. Biol.*, 1965, 13, pp. 238–252.

Huang et al., "Interaction of the N–terminus of Sterol Carrier Protein 2 with Membranes: Role of Membrane Curvature", *Biochem. J*, 1999, vol. 8, pp. 593–603.

Gregoriadis, Gregory, "The Carrier Potential of Liposomes in Biology and Medicine", *New Engl. J. Med.*, 1976, vol. 295, No. 13, pp. 704–710.

Cudd et al., "Liposomes Injected Intravenously into Mice Associate with Liver Mitochondria," *Biochem. Biophys Acta*, 1984, vol. 774, pp. 169–180.

Benz et al., "Electrical Capacity of Black Lipid Films and of Lipid Bilayers Made from Monolayers", *Biochem. Biophys. Acta*, 1975, vol. 394, pp. 323–334.

Goodman and Gillman's, "The Pharmacological Basis of Therapeutics," $7^{th}$ Ed., *MacMillan Publishing Co.*, New York (1985), Chap. 15, p. 312.

Cherney, L.S., "Tetracaine Hydroiodide: A Long Lasting Local Anesthetic Agent for the Relief of Postoperative Pain", *Anesth. Analg.*, 1963, vol. 42, No. 4, pp. 477–481.

Haynes et al., "Metal–Ligand Interactions in Organic Chemistry and Biochemistry", B. Pullman and N. Goldblum (eds.), part 2, 1977, pp. 189–212.

Haynes et al., "Ultra–Long Duration Local Anesthesia Produced by Injection of Lecithin–coated Methxyfluorene Microdroplets", *Aneshesiology*, 1985, vol. 63, No. 5, pp. 490–499.

Haynes et al., "Ultra–Long Duration Local Anesthesia Produced by Intra–Dermal Injection of Lecithin–Coated Methoxyflurane Microdroplets", *Proceed. Intern. Symp. Control. Rel. Bioact. Mater.*, 1987, vol. 14, pp. 293–294.

Kirkpatrick et al., "Local Anesthetic Efficacy of Methyoxyflurane Microdroplets in Man," *Anesthesiology*, 1987, vol. 67(3A0, p. A254.

Wu et al., "Pharmacokinetics of Methyoxyflurane After Its Intra–Dermal Injection as Lecithin–Coated Microdroplets," *Journal of Controlled Release* (in press), 1989, vol. 9, pp. 1–12.

Pompp's Chemie Lexikon, (Dr. Hermann Rompp), "Emulsion", 2 Aufl., Bd. 1, Stuttgart (1950).

Bergmann, Ludwig, *Der Ultraschall*, 5 Aufl., Stuttgart (1949), S. 551–564, 672f.

Sheu et al., "Characterization and Dissolution of Fenofibrate Solid Dispersion Systems"; *Int. J. Pharm*, 1994, vol. 103(2), pp. 137–146.

* cited by examiner

WATER-INSOLUBLE DRUG PARTICLE PROCESS

This claims the benefit of provisional application 60/198,579 filed on Apr. 20, 2000.

BACKGROUND OF THE INVENTION

The present invention relates to an improved process for the preparation of small particles containing a poorly water soluble drug, and in particular to an improved process for the preparation of small particles containing a poorly water soluble drug as a dispersion in an aqueous carrier and as dried small particles containing a poorly water soluble drug.

There is a critical need in the pharmaceutical and other biological based industries to formulate industrially useful water-insoluble or poorly water soluble substances into formulations for oral, injectable, inhalation, ophthalmic, and other routes of delivery. Industrially useful water insoluble or poorly water soluble substances include water insoluble or poorly water soluble biologically useful compounds, imaging agents, pharmaceutically useful compounds and in particular water insoluble and poorly water soluble drugs for human and veterinary medicine.

Microparticles of water insoluble or poorly soluble substances are small particles having diameters of from nanometers to micrometers and refer to solid particles of irregular, non-spherical or spherical shapes. When the insoluble and poorly soluble substances are therapeutically and diagnostically useful substances, formulations containing them as microparticles or small particles provide some specific advantages over unformulated non-micronized drug particles. These advantages include improved oral bioavailability of drugs that are poorly absorbed from the GI tract, development of injectable formulations that are currently available only in oral dosage form, less toxic injectable formulations that are currently prepared with organic solvents, sustained release of intramuscular injectable drugs that are currently administered through daily injection or constant infusion, preparation of inhaled, ophthalmic formulation of drugs that otherwise could not be formulated for nasal or ocular use, as well as other advantages.

Current technology for delivering insoluble drugs as described in U.S. Pat. Nos. 5,091,188; 5,091,187 and 4,725,442 focuses on (a) either coating small drug particles with surface active substances that are natural or synthetic phospholipids or (b) dissolving the drug in a suitable lipophilic carrier and forming an emulsion stabilized with surface active substances that are natural or semisynthetic phospholipids. One of the characteristics of these formulations is that certain drug particles in suspension tend to grow over time because of the dissolution and reprecipitation phenomenon known as the "Oswald ripening".

U.S. Pat. No. 5,145,684 discloses methods for preparation and dispersions of particles consisting of crystalline drug substance having a surface modifier or surface active substance adsorbed to maintain an effective average particle size of less than about 400 nm. However, the method requires a milling step that can result in impurities being added to the formulation from fractured milling media.

U.S. Pat. Nos. 5,470,583 and 5,336,507 disclose methods for preparation of nanoparticles using a charged phospholipid as a cloud point modifier.

U.S. Pat. No. 5,302,401 discloses compositions and methods for forming nanoparticles with a surface modifier and a cryoprotectant adsorbed thereon.

International Patent Application WO 99/39700 describes the preparation of submicron nanoparticles from a pharmacologically active principle and a composite material consisting of at least one lipidic substance and at least one amphiphilic substance using high pressure homogenization to form a microemulsion of the composite material at a temperature higher than the melting temperature of at least one of the materials forming the composite and in the presence of one or more aqueous surfactants as surface active substances and then cooling the microemulsion to form a dispersion of solid particles.

U.S. Pat. No. 5,785,976 discloses a heated aqueous emulsification and cooling process for the preparation of solid lipid particles. In that process a solid lipid or bioactive agent or a mixture of solid lipids or bioactive agents is melted and stabilizers, i.e., surface active substances, are added either to the lipid or bioactive agent and to the aqueous phase or to the aqueous phase only. The aqueous phase is heated to the temperature of the melt before mixing and may contain stabilizers, isotonicity agents, buffering substances, cryoprotectants and/or preservatives. The molten lipid compounds and the bioactive agents can be emulsified in the aqueous phase by high-pressure homogenization. The homogenized dispersion is then allowed to cool until solid particles are formed by recrystallization of the dispersed agents. Drugs or other bioactive substances to be incorporated into the particles may be melted together with the lipids or may be dissolved, solubilized or dispersed in the lipid melt before an emulsification by homogenization step.

U.S. Pat. No. 5,922,355 discloses a method for preparing submicron size microparticles by particle size reduction methods in which a solid material is reduced in size over a period of time while continuously below the melting point of the material or by precipitation while the particles are stabilized with phospholipids as surface active substances in combination with other surface modifiers to control growth of particle size and enhance storage stability. The use of one or more surface modifiers in addition to a phospholipid provides volume weighted mean particle size values that are much smaller than what can be achieved using phospholipid alone without the use of an additional surface active substance (surfactant) with the same energy input while providing compositions resistant to particle size growth on storage. The phospholipid and the surfactant are both present at the time of particle size reduction.

In one aspect while it is advantageous in very many cases to use particulate pharmaceutical formulations wherein particle sizes are stabilized by combinations of phospholipids and surface modifiers according to U.S. Pat. No. 5,922,355, it is sometimes desirable to produce pharmaceutical formulations or pre-formulations which are stabilized by biocompatible phospholipids without the use of additional surface active substances. This can be desirable, for example, when there is a subsequent need to modify the composition of a particle-containing formulation in a step following the formation of the particles such as by the addition of one or more additional ingredients that are not compatible with additional surface modifiers shown to be beneficial in U.S. Pat. No. 5,922,355, the disclosure of which is hereby incorporated by reference. In one aspect it is therefore desirable to produce drug particles stabilized by one or more phospholipids in the absence of additional surface modifiers but which exhibit enhanced stability toward particle growth and which maintain sub-micron and micron size particles on subsequent storage as suspension or solid dosage form.

In another aspect, particle size reduction methods such as those disclosed in U.S. Pat. No. 5,922,355 in which particles of a material are reduced in size in the presence of phospholipid and another surface active substance while the material is maintained in the solid phase require processing for a certain length of time to achieve a desired particle size. The time is directly related to the number of homogenization volume passes or turnovers performed on a volume of a suspension of particles in a size reduction process. It is desirable to further reduce that length of time by providing an improved process that can decrease the overall number of turnovers to achieve a desired particle size.

Fenofibrate or 2-[4-(4-chlorobenzoyl)phenoxy]-2-methyl-propanoic acid 1-methylethyl ester is an example of a poorly water soluble compound. It is a benzophenone containing a para-chlorophenyl group and a para-isopropyloxycarbonylisopropoxyphenyl group, both of which are substantially hydrophobic groups. Fenofibrate exhibits a melting point reported to be in the range of 79 to 82° C. (Physician's Desk Reference, 1999 Edition, page 477), which is above that of the symmetrically unsubstituted benzophenone with a reported melting point range of 48 to 51° C. but below that of the symmetrically substituted 4,4'-dichlorobenzophenone with a reported range of 144 to 146° C. (Aldrich Chemical Co. catalog, 1999).

Fenofibrate acts as a potent lipid modulator agent offering unique and significant clinical advantages over existing products in the fibrate class of drugs. Fenofibrate produces substantial reductions in plasma triglyceride levels in hyper-triglyceridemic patients and in plasma cholesterol and LDL-cholesterol in hypercholesterolemic and mixed dyslipidemic patients.

Fenofibrate is a prodrug that is absorbed and then hydrolyzed by tissue and plasma esterases to fenofibric acid, its active metabolite. Fenofibric acid, responsible for the pharmacological activity, has a plasma half-life of about 20 hours. Fenofibrate is a poorly water soluble drug and is practically insoluble in water. It is normally poorly and variably absorbed, and has to be taken with food.

Fenofibrate was first available in a pharmaceutical dosage form (LIPIDIL®) consisting of a hard gelatin capsule containing fenofibrate, lactose, pregelatinized starch and magnesium stearate. After oral administration, during a meal, about 60% of the dose of this conventional form is effectively absorbed and found in the blood as fenofibric acid (Weil et al., The metabolism and disposition of 14C-fenofibrate in human volunteers, Drug. Metabol. Dispos. Biol. Fate. Chem., 18(1990) 115–120).

Historically, in order to improve the intestinal absorption, another pharmaceutical dosage form was introduced (LIPIDIL Micro). European Patent Application 330,532 and U.S. Pat. No. 4,895,726 disclose a fenofibrate composition in which the fenofibrate powder is co-micronized with a solid wetting agent. Sodium lauryl sulfate is described as the wetting agent of choice. The co-micronized powder so obtained is mixed with capsule filling excipients such as lactose, starch, cross-linked polyvinyl pyrrolidone (PVP), and magnesium stearate. A study comparing this formulation (LIPIDIL Micro) to the conventional form (LIPIDIL) had showed statistically significant increase in bioavailability with the former.

European Patent Application 724,877 describes fenofibrate powder co-micronized with a wetting agent in association with a vitamin E component (tocopherol and/or its organic acid ester) for treating or preventing disorders associated with lipoprotein oxidation.

U.S. Pat. No. 4,800,079 describes a medicinal composition in the form of granules with controlled release of fenofibrate. Each granule includes an inert core, a layer based on fenofibrate and a protective layer. Fenofibrate is present in the form of crystalline microparticles of dimensions not greater than 30 μm.

U.S. Pat. No. 4,961,890 describes a process for preparing a controlled release formulation containing fenofibrate in an intermediate layer in the form of crystalline microparticles (less than 30 μm in diameter) within a multilayer inert matrix.

U.S. Pat. No. 5,545,628 describes a pharmaceutical composition for treating hyperlipidemia or hypercholesterolemia or both in a mammal, by providing an effective amount of each of fenofibrate and an excipient including one or more polyglycolyzed glycerides.

European Patent Application 757,911 describes a fenofibrate pharmaceutical dosage form in which fenofibrate is in solution in diethylene glycol monoethyl ether (EMDG) which is a non-ionic surfactant.

European Patent Application 904,781 describes a process for making granules of a solid dispersion of a disintegrant in molten fenofibrate by blending a solid dispersing agent into molten fenofibrate, cooling and solidifying the bulk mixture in a tray, and then milling the solid through a screen to produce granules. Disintegrants include polymers such as starch, croscarmellose sodium, sodium starch glycolate, and crospovidone. Such disintegrants are slow to swell and dissolve in aqueous media. Furthermore, when crosslinked as in the case of crospovidone, a polymeric disintegrant will not be uniformly dissolved in molten drug but rather at best will form micro-domains in molten fenofibrate. In addition, polymeric materials can exhibit phase separation phenomena when distributed in a substance with which there is not complete compatibility. This was shown, in part, by Sheu, M. T. et al., "Characterization and dissolution of fenofibrate solid dispersion systems", Int. J. Pharm. (1994), 103(2), 137–46 using differential scanning calorimetry measurements that found fenofibrate to be incompatible with poly(vinyl pyrrolidone). Thus, preparation of a bulk mixture in the melt followed by solidification and grinding can lead to non-uniform distributions and compositions in granules. This can adversely effect the bioavailability of the active component.

U.S. Pat. No. 5,700,471 relates to a process for the micronization of compounds having low solubility in water by exposing such compounds briefly to a temperature above their respective melting points, dispersing them with turbulence in an aqueous or organic phase, and subsequently cooling the phase to form a fine particle dispersion. However, it is specified (column 2, lines 1–9) that certain substances and specifically fenofibrate are not amenable to processing entirely without organic solvents because their aqueous dispersions agglomerate and cannot be metered. Thus, in example 2 of U.S. Pat. No. 5,700,471, fenofibrate is not directly dispersed in water but rather is first dissolved in a four-fold excess of a water-miscible organic solvent (isopropanol) which must be removed in a subsequent step. Organic solvents can pose flammability risks, exposure dangers to process operators, potential environmental problems, and added expense related to their storage, ultimate removal from a formulation, and disposal. Thus it is desirable to overcome the use of organic solvents where possible.

U.S. Pat. No. 4,880,634 describes a method of production of an excipient system containing a pharmacologically active substance for peroral administration comprised of lipid nano-pellets in an aqueous, colloidal suspension. The method comprises forming a melt of a mixture of at least one surfactant, a pharmacologically active substance, and at least one lipid, dispersing the molten mixture within an aqueous solution at a temperature above the melting point of the lipid to form lipid nano-pellets, and cooling the suspension below the melting point of the lipid. In the process, a pharmacologically effective substance is thoroughly dissolved in the lipid or mixture of lipids during the preparation of the lipid nano-pellets. Animal and plant phospholipids such as lecithin and their hydrogenated forms may be employed in the process although the use of chloroform is taught in examples citing PHOSPHOLIPON™ 100H. The pharmacologically effective substance can be added to the melted lipid in molten form or dissolved or dispersed in the molten lipid.

BRIEF SUMMARY OF THE INVENTION

We have found that small particles containing a poorly water soluble drug can be prepared by a process comprising the steps of (a) mixing at high shear an admixture of a poorly water soluble drug and one or more than one surface active substance in an aqueous carrier in the absence of an organic solvent within a first temperature range at or above the melting point of the poorly water soluble drug to form a heated suspension containing the drug, then (b) homogenizing said heated suspension in a first pressure range and within said first temperature range to form a heated homogenate containing the drug, then (c) cooling said heated homogenate to a second temperature range below the melting temperature of the poorly water soluble drug to form a transiently stable cooled homogenate containing the drug, then (d) applying a particle stabilizing energetic process to said cooled homogenate within a second temperature range below the melting point of the drug and in a second pressure range to form a cooled dispersion of stabilized small particles containing the drug, and then (e) optionally drying the cooled dispersion to form dried small particles containing the poorly water soluble drug.

Particularly important to this invention is the use of two homogenization steps separated by a cooling step. The first homogenization step is done on a heated suspension having the poorly water soluble drug in a molten phase in the presence of one or more than one surface active substance to provide a heated homogenate containing the drug. The heated homogenate is usually in the form of a microemulsion comprising small molten particles or droplets of drug stabilized by one or more than one surface active substance. The heated homogenate containing the drug is then cooled to provide a transiently stable cooled homogenate containing the drug. The transiently stable cooled homogenate comprises small particles of drug in which the drug is in a solid phase which may be amorphous, crystalline, or a combination of both. The small particles of the cooled homogenate are stabilized by the surface active substance or substances but the particles are transiently stable with respect to particles size growth and eventual precipitation of solid drug from the aqueous carrier.

The second homogenization step is done on the cooled homogenate after a cooling step to produce a cooled dispersion of small particles containing the drug and having greater stability to particle growth and precipitation than the cooled homogenate. The second homogenization step is a stabilizing energetic process. It provides small particles that are more stable than the transiently stable particles of the cooled homogenate prepared in the first homogenization step and prevents relatively large crystals and/or agglomerates of the poorly water soluble drug from forming. The second homogenization step thereby facilitates the formation of stabilized small particles of the poorly water soluble drug. It also provides overall rapid formation of desired small particles containing the poorly water soluble drug. Optionally, the small particles can be isolated by a drying process, for example by lyophilization or by spray drying. Thus, the process can provide dried small particles containing a poorly water soluble drug. In the absence of the second homogenization step, very large amounts of the poorly water soluble drug can precipitate from the transiently stable aqueous cooled homogenate or can form a sediment by precipitation from the aqueous carrier.

In one aspect of this invention, we have unexpectedly found that small particles containing the poorly water soluble drug fenofibrate can be prepared by a process comprising the steps of (a) mixing at high shear an admixture of fenofibrate and one or more than one surface active substance in an aqueous carrier in the absence of an organic solvent within a first temperature range above the melting point of fenofibrate to form a heated suspension containing fenofibrate, then (b) homogenizing said heated suspension in a first pressure range and within said first temperature range to form a heated homogenate containing fenofibrate, then (c) cooling said heated homogenate to a second temperature range below the melting temperature of fenofibrate to form a transiently stable cooled homogenate containing fenofibrate, then (d) applying a particle stabilizing energetic process to said cooled homogenate within a second temperature range and in a second pressure range to form a cooled dispersion of stabilized small particles containing fenofibrate, and then (e) optionally drying the cooled dispersion to form dried small particles containing fenofibrate. Particularly important to this aspect of the invention is the use of two homogenization steps separated by a cooling step and the use of a phospholipid as a surface active substance. The first homogenization step is done on a heated suspension in the presence of a phospholipid as a surface active substance, in the absence of an organic solvent, and wherein fenofibrate is molten to provide a homogenized microemulsion containing fenofibrate. The second homogenization step is done on a transiently stable cooled homogenate in the presence of the phospholipid and wherein the fenofibrate is a solid to provide a homogenized dispersion of small particles containing fenofibrate. In the absence of the second homogenization step, relatively large crystals of fenofibrate readily form from the transiently stable cooled homogenate. In the absence of a heated first homogenization step on the molten drug, homogenization of solid fenofibrate to provide a suspension of small particles of fenofibrate takes a prolonged or much longer time in the same homogenization apparatus under substantially the same homogenization conditions of pressure and temperature relative to the time taken in the second homogenization step of this invention.

It is an advantage of this invention that small particles containing a poorly water soluble drug stabilized with one or more than one surface active substances can be prepared as a dispersion in an aqueous carrier or as dried small particles.

It is another advantage of this invention that small particles containing a poorly water soluble drug can be prepared in the absence of an organic solvent.

It is another advantage of this invention that small particles containing a poorly water soluble drug can be prepared using pharmaceutically acceptable excipients such as phospholipids, sugars and polyols.

It is a further advantage of this invention that a suspension of small particles containing a poorly water soluble drug can be prepared which suspension is relatively stable to mechanical agitation and to growth of larger crystals of the drug over a period of time.

It is another advantage of this invention that small particles containing fenofibrate can be prepared without the use of an organic solvent.

It is a further advantage of this invention that a suspension of small particles containing fenofibrate can be prepared which suspension is relatively stable to mechanical agitation and to growth of larger crystals of the drug over a period of time.

DETAILED DESCRIPTION OF THE INVENTION

The present invention relates to an improved process for the preparation of small particles containing a poorly water soluble drug, and in particular to an improved process for the preparation of small particles containing a poorly water soluble drug as a dispersion in an aqueous carrier and as dried small particles containing a poorly water soluble drug.

As used herein, "small particle" refers to a particle or a distribution of particles having a diameter or an average diameter, respectively, of from nanometers to micrometers. Small particles are microparticles, as used herein, and also refer to solid particles of irregular, non-spherical or spherical shapes.

By "dried" we mean having a water or moisture content greater than zero percent and below 5% by weight, preferably below 4% by weight, more preferably below 3% by weight, and even more preferably below 2% by weight, and most preferably below 1% by weight. In preferred embodiments, the amount of water is between 0.1% and 3%, more preferably between 0.1% and 2%, and most preferably between 0.1% and 1% by weight. By "anhydrous" we mean have zero water content.

Formulations containing these small particles or microparticles provide some specific advantages over unformulated non-micronized drug particles. These advantages include improved oral bioavailability of drugs that are poorly absorbed from the GI tract, development of injectable formulations that are currently available only in oral dosage form, less toxic injectable formulations that are currently prepared with organic solvents, sustained release of intramuscular injectable drugs that are currently administered through daily injection or constant infusion, and preparation of inhaled and ophthalmic formulations of drugs that otherwise could not be formulated for nasal or ocular use.

By "transiently stable" we mean that the small particles of the cooled homogenate remain as small particles in a dispersion of the aqueous carrier at the size finally produced in the first homogenization step for a relatively short period of time and not indefinitely. The period of time that a cooled homogenate remains transiently stable can vary from up to about one second to up to about 48 hours, and preferably from up to about 15 minutes to up to about 24 hours, and most preferably from up to about 6 hours to up to about 24 hours although though the period of time can vary with many factors. For example as commonly seen in recrystallization of a crystalline substance from an organic solvent, the growth and precipitation of crystals can be induced or enhanced by the presence of seed crystals, by stirring of a cooled supersaturated solution of drug, and by scratching the internal surface of a vessel containing supersaturated dissolved drug below the level of the liquid thereby creating nucleation sites for crystallization. Such crystal growth is not desirable in the present invention. The transiently stable particles can grow slightly in size (i.e., in average diameter) over the relatively short period of time by as much as 1000% of their original size or more from that size produced in the heated homogenization step, but preferably will remain at the size at which they were produced in the first homogenization step up to a size about 100% larger in diameter, and more preferably up to a size about 50% larger in diameter. After the relatively short period of time, the particles will continue to become larger such as by Ostwald ripening and crystallization. After the relatively short period of time, drug may also crystallize in the form of large particles from the suspension. The particles of the heated homogenate may also irreversibly agglomerate after the relatively short period of time. Additionally, after the relatively short period of time, the components of the formulation may phase separate from the aqueous carrier and optionally precipitate and separate into components that contain largely drug and largely surface active substance.

Water insoluble and poorly water soluble compounds are those having poor solubility in water at or below normal physiological temperatures, that is <5 mg/ml at physiological pH (6.5–7.4). Preferably their water solubility is <1 mg/ml, and more preferably <0.1 mg/ml. It is desirable that the drug be stable in water as a dispersion. Otherwise or in addition a dried form such as a lyophilized or spray-dried solid form may be desirable for example for use in formation of drug delivery compositions including capsules, tablets, and formulations with additional excipients and drugs.

Examples of some preferred water-insoluble drugs include immunosuppressive and immunoactive agents, antiviral and antifungal agents, antineoplastic agents, analgesic and anti-inflammatory agents, antibiotics, anti-epileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antarrhythmics, antihypertensive agents, antineoplastic agents, hormones, and nutrients. A detailed description of these and other suitable drugs may be found in Remington's Pharmaceutical Sciences, 18th edition, 1990, Mack Publishing Co. Philadelphia, Pa. which is hereby incorporated by reference.

Drugs that are poorly soluble in water can have pharmaceutical efficacy in a number of therapeutic and diagnostic imaging areas. Non-limiting classes of compounds and agents from which poorly water soluble drugs that melt without decomposition and are useful in this invention can be selected include anesthetic agents, ace inhibiting agents, antithrombotic agents, anti-allergic agents, antibacterial agents, antibiotic agents, anticoagulant agents, anticancer agents, antidiabetic agents, antihypertension agents, antifungal agents, antihypotensive agents, antiinflammatory agents, antimicotic agents, antimigraine agents, antiparkinson agents, antirheumatic agents, antithrombins, antiviral agents, beta blocking agents, bronchospamolytic agents, calcium antagonists, cardiovascular agents, cardiac glycosidic agents, carotenoids, cephalosporins, contraceptive agents, cytostatic agents, diuretic agents, enkephalins, fibrinolytic agents, growth hormones, immunosupressants, insulins, interferons, lactation inhibiting agents, lipid-lowering agents, lymphokines, neurologic agents, prostacyclins, prostaglandins, psycho-pharmaceutical agents, protease inhibitors, magnetic resonance diagnostic imaging agents, reproductive control hormones, sedative agents, sex hormones, somatostatins, steroid hormonal agents, vaccines, vasodilating agents, and vitamins.

Preferred drugs suitable for use in this invention melt without decomposition in admixtures, suspensions, dispersions, and homogenates of this invention, preferably in a temperature range from about physiological temperature 37° C. to about 275° C., and more preferably in a temperature range from just above physiological temperature, about 40° C., to about 230° C. In one aspect of this invention, preferred suitable drugs melt without decomposition in the range from physiological temperature at about 37° C. to the boiling point of water at atmospheric pressure, i.e., up to about 100° C. but not including 100° C. In this case, the aqueous carrier can be maintained at the first temperature range generally without the need of pressurization to maintain the aqueous carrier as a liquid during the heated homogenization process. In another aspect of this invention, preferred suitable drugs melt without decomposition in the range from at the boiling point of the aqueous carrier under ambient pressure, i.e., from 100° C. up to 275° C. In this case, the aqueous carrier can be maintained at the first temperature range generally by using a pressurized apparatus to maintain the aqueous carrier as a liquid during the heated homogenization process. Of course, if desired, a pressurized apparatus can be used in the range below the boiling point of the aqueous carrier such as in the region of from 50° C. to about 100° C., and the aqueous carrier will also be maintained as a liquid.

Non-limiting examples of representative poorly soluble drugs that melt without decomposition in admixtures, suspensions, dispersions, and homogenates of this invention at temperatures at or below 275° C. can be selected from the group consisting albendazole (m.p. 208–21° C.), albendazole sulfoxide, alfaxalone (m.p. 172–174° C.), acetyldigoxin, acyclovir analogs melting at or below 275° C., alprostadil, aminofostin, anipamil, antithrombin III, atenolol (m.p. 146–148° C.), azidothymidine, beclobrate (m.p. 200–204° C.), beclomethasone (m.p. 117–120° C.), belomycin, beuzocaine (m.p. 88–90° C.) and derivatives, beta carotene (m.p. 183° C.), beta endorphin, beta interferon, bezafibrate (m.p. 186° C.), binovum, biperiden (m.p. 112–116° C.), bromazepam (m.p. 237–238° C.), bromocriptine, bucindolol, buflomedil (m.p. 192–193° C.), bupivacaine (m.p. 107–108° C.), busulfan (m.p. 114–118° C.), cadralazine (m.p. 160–162° C.), campotothecin (m.p. 264–267 and 275° C.), canthaxanthin (m.p. 217° C.), captopril (m.p. 103–104° C.), carbamazepine (m.p. 190–193° C.), carboprost, cefalexin, cefalotin, cefamandole (m.p. 190° C.), cefazedone, cefluoroxime, cefirienoxime, cefoperazone (m.p. 169–171° C.), cefotaxime, cefoxitin (m.p. 149–150° C.), cefsulodin (m.p. 175° C.), ceftizoxime, chiorambucil (m.p. 64–66° C.), chromoglycinic acid, ciclonicate (m.p. 127–128° C.), ciglitazone, clonidine (m.p. 130° C.), cortexolone, corticosterone (m.p. 180–182° C.), cortisol (m.p. 212–220° C.), cortisone (m.p. 220–224° C.), cyclophosphamide (m.p. 41–45° C.), cyclosporin A (m.p. 148–151° C.) and other cyclosporins, cytarabine (m.p. 212–213° C.), desocryptin, desogestrel (m.p. 109–110° C.), dexamethasone esters such as the acetate (m.p. 238–240° C.), dezocine, diazepam (m.p. 125–126° C.), diclofenac, dideoxyadenosine (m.p. 160–163° C.), dideoxyinosine, digitoxin (m.p. 256–257° C.), digoxin, dihydroergotamine (m.p. 239° C.), dihydroergotoxin, diltiazem (m.p. 207–212° C.), dopamine antagonists, doxorubicin (m.p. 229–231° C.), econazole (m.p. 87° C.), endralazine (m.p. 185–188° C.), enkephalin, enalapril (m.p. 143–145° C.), epoprostenol, estradiol (m.p. 173–179° C.), estramustine (m.p. 104–105° C.), etofibrate (m.p. 100° C.), etoposide (m.p. 236–251° C.), factor ix, factor viii, felbamate (m.p. 151–152° C.), fenbendazole (m.p. 233° C.), fenofibrate (m.p. 79–82° C.), flunarizin (m.p. 252° C.), flurbiprofen (m.p. 110–111° C.), 5-fluorouracil (m.p. 282–283° C.), flurazepam (m.p. 77–82° C.), fosfomycin (m.p. 94° C.), fosmidomycin, furosemide (m.p. 206° C.), gallopamil, gamma interferon, gentamicin (m.p. 102–108° C.), gepefrine (m.p. 155–158° C.), gliclazide (m.p. 180–182° C.), glipizide (m.p. 208–209° C.), griseofulvin (m.p. 220° C.), haptoglobulin, hepatitis B vaccine, hydralazine (m.p. 172–173° C.), hydrochiorothiazide (m.p. 273–275° C.), hydrocortisone (m.p. 212–220° C.), ibuprofen (m.p. 75–77° C.), ibuproxam (m.p. 119–121° C.), indinavir, indomethacin (m.p. 155° C.), iodinated aromatic x-ray contrast agents melting below 275° C. such as iodamide (m.p. 255–257° C.), ipratropium bromide (m.p. 230–232° C.), ketoconazole (m.p. 146° C.), ketoprofen (m.p. 94° C.), ketotifen (m.p. 152–153° C.), ketotifen fumarate (m.p. 192° C.), K-Strophanthin (m.p. 175° C.), labetalol, lactobacillus vaccine, lidocaine (m.p. 68–69° C.), lidoflazine (m.p. 159–161° C.), lisuride (m.p. 186° C.), lisuride hydrogen maleate (m.p. 200° C.), lorazepam (m.p. 166–168° C.), lovastatin, mefenamic acid (m.p. 230–231° C.), meiphalan (m.p. 182–183° C.), memantine, mesulergin, metergoline (m.p. 146–149° C.), methotrexate (m.p. 185–204° C.), methyldigoxin (m.p. 227–231° C.), methyiprednisolone (m.p. 228–237° C.), metronidazole (m.p. 158–160° C.), metisoprenol, metipranolol (m.p. 105–107° C.), metkephamide, metolazone (m.p. 253–259° C.), metoprolol, metoprolol tartrate, miconazole (m.p. 135° C.), miconazole nitrate (m.p. 170 and 185° C.), minoxidil (m.p. 248° C.), misonidazol, molsidomine, nadolol (m.p. 124–136° C.), nafiverine (m.p. 220–221° C.), nafazatrom, naproxen (m.p. 155° C.), natural insulins, nesapidil, nicardipine (m.p. 168–170° C.), nicorandil (m.p. 92–93° C.), nifedipine (m.p. 172–174° C.), niludipin, nimodipine, nitrazepam (m.p. 224–226° C.), nitrendipine, nitrocamptothecin, 9-nitrocamptothecin, oxazepam (m.p. 205–206° C.), oxprenolol (m.p. 78–80° C.), oxytetracycline (m.p. 181–182° C.), penicillins such as penicillin G benethamine (m.p. 147–147° C.), penecillin O (m.p. 79–81° C.), phenylbutazone (m.p. 105° C.), picotamide, pindolol (m.p. 171–173° C.), piposulfan (m.p. 175–177° C.), piretanide (m.p. 225–227° C.), piribedil (m.p. 98° C.), piroxicam (m.p. 198–200° C.), pirprofen (m.p. 98–100° C.), plasminogenic activator, prednisolone (m.p. 240–241° C.), prednisone (m.p. 233–235° C.), pregneninolone (m.p. 193° C.), procarbazine, procaterol, progesterone (m.p. 121° C.), proinsulin, propafenone, propentofylline, propofol, propranolol (m.p. 96° C.), rifapentine, simvastatin, semi-synthetic insulins, sobrerol (m.p. 130° C.), somatostatin and its derivatives, somatotropin, stilamin, sulfinalol whose hydrochloride melts at 175° C., sulfinpyrazone (m.p. 136–137° C.), suloctidil (m.p. 62–63° C.), suprofen (m.p. 124° C.), suiprostone, synthetic insulins, talinolol (m.p. 142–144° C.), taxol, taxotere, testosterone (m.p. 155° C.), testosterone propionate (m.p. 118–122° C.), testosterone undecanoate, tetracane HI (m.p. ~450° C.), tiaramide (HCl m.p. 159–161° C.), tolmetin (m.p. 155–157° C.), tranilast (m.p. 211–213° C.), triquilar, tromantadine (HCl m.p. 157–158° C.), urokinase, valium (m.p. 125–126° C.), verapamil (m.p. 243–246° C.), vidarabine, vidarabine phosphate sodium salt, vinblastine (m.p. 211–216° C.), vinburin, vincamine (m.p. 232–233° C.), vincristine (m.p. 218–220° C.), vindesine (m.p. 230–232° C.), vinpocetine (m.p. 147–153° C.), vitamin A (m.p. 62–64° C.), vitamin E succinate (m.p. 76–78° C.), and x-ray contrast agents. Drugs can be neutral species or basic or acidic as well as salts such as exist in the presence of an aqueous buffer.

Examples of some suitable surface active substances that are useful in this invention include: (a) natural surfactants such as casein, gelatin, tragacanth, waxes, enteric resins, paraffin, acacia, gelatin, cholesterol esters and triglycerides, (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, polyvinyl alcohol, polyvinylpyrrolidone, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylarnmonium bromide, chitosans and lauryldimethylbenzylammonium chloride, (e) colloidal clays such as bentonite and veegum. A detailed description of these surfactants may be found in Remington's Pharmaceutical Sciences, and Theory and Practice of Industrial Pharmacy, Lachman et al, 1986.

More specifically, examples of suitable surface active substances include one or a combination of the following: polaxomers, such as PLURONIC™ F68, F108 and F127, which are block copolymers of ethylene oxide and propylene oxide available from BASF, and poloxamines, such as TETRONIC™ 908 (T908), which is a tetrafunctional block copolymer derived from sequential addition of ethylene oxide and propylene oxide to ethylene-diamine available from BASF, TRITON™ X-200, which is an alkyl aryl polyether sulfonate, available from Rohm and Hans. TWEEN™ 20, 40, 60 and 80, which are polyoxyethylene sorbitan faffy acid esters, available from ICI Speciality Chemicals, CALRBOWAX™ 3550 and 934, which are polyethylene glycols available from Union Carbide, hydroxypropylmethylcellulose, dimyristoyl phosphatidylglycerol sodium salt, sodium dodecylsulfate, sodium deoxycholate, and cetyltrimethylammonium bromide.

Preferred surface active substances are phospholipid surface active substances and mixtures comprising phospholipid surface active substances. Suitable phospholipids include animal and plant phospholipids; egg phospholipids; soya bean phospholipids; corn phospholipids; wheat germ, flax, cotton, and sunflower seed phospholipids; milk fat phospholipids; glycerophospholipids; sphingophospholipids; phosphatides; phospholipids containing fatty acid esters including palmitate, stearate, oleate, linoleate, and arachidonate which esters can be mixtures and mixtures of isomers in the phospholipids; phospholipids composed of fatty acids containing one or more than one double bond such as dioleoyl phosphatidylcholine and egg phosphatidylcholine that are not stable as powders but are hygroscopic and can absorb moisture and become gummy; phospholipids composed of saturated fatty acids that are stable as powders and are less amenable to absorption of moisture; phosphatidylserines; phosphatidylcholines; phosphatidylethanolamines; phosphatidylinositols; phosphatidylglycerols such as dimyristoyl phosphatidyiglycerol, L-alpha-dimyristoyl phosphatidylglycerol also known as 1,2-dimyristoyl-sn-glycero-3-phospho(rac-1-glycerol) and also known as DMPG; phosphatidic acid; hydrogenated natural phospholipids; and commercially available phospholipids such as those available from Avanti Polar Lipids, Inc. of Alabaster, Ala., USA. In the absence of an internal counterion in the phospholipid, a preferred counterion is a monovalent cation such as sodium ion. The phospholipid may be salted or desalted, hydrogenated, partially hydrogenated, or unsaturated, natural, synthetic, or semisynthetic.

Preferred phospholipids include LIPOID™ E80, LIPOID EPC, LIPOID SPC, DMPG, PHOSPHOLIPON 100H a hydrogenated soybean phosphatidylcholine, PHOSPHOLIPON 90H, LIPOID SPC-3, and mixtures thereof. A currently most preferred phospholipid is LIPOID E80.

The concentration of surface active substance added to the formulations prepared according to this invention can be present in the range of 0.1 to 50%, preferably 0.2 to 20%, and more preferably 0.5 to 10%.

In a preferred aspect, the present invention is directed to a process for the preparation of small particles containing a poorly water soluble drug and a phospholipid surface stabilizing substance, and comprises the steps of (a) mixing at high shear an admixture of the poorly water soluble drug and a phospholipid substance in an aqueous carrier in the absence of an organic solvent and optionally in the presence of one or more than one surface active substances within a first temperature range at or above the melting point of the drug to form a heated suspension containing the drug, then (b) homogenizing said heated suspension in a first pressure range and within said first temperature range to form a heated homogenate containing the drug, then (c) cooling said heated homogenate to a second temperature range below the melting temperature of the drug to form a transiently stable cooled homogenate containing the drug, then (d) applying a particle stabilizing energetic process to said cooled homogenate within a second temperature range and in a second pressure range to form a cooled dispersion of stabilized small particles containing the drug, and then (e) optionally drying the cooled dispersion to form dried small particles containing the drug.

In a specific aspect, the present invention is directed to a process for the preparation of small particles containing the poorly water soluble drug, fenofibrate. The process comprises the steps of (a) mixing at high shear an admixture of the poorly water soluble drug fenofibrate and a phospholipid substance in an aqueous carrier in the absence of an organic solvent and optionally in the presence of one or more than one surface active substances within a first temperature range at or above the melting point of the drug to form a heated suspension containing the drug, then (b) homogenizing said heated suspension in a first pressure range and within said first temperature range to form a heated homogenate containing the drug, then (c) cooling said heated homogenate to a second temperature range below the melting temperature of the drug to form a transiently stable cooled homogenate containing the drug, then (d) applying a particle stabilizing energetic process to said cooled homogenate within a second temperature range and in a second pressure range to form a cooled dispersion of stabilized small particles containing the drug, and then (e) optionally drying the cooled dispersion to form dried small particles containing the drug.

An admixture of a poorly water soluble drug and a surface active substance such as a phospholipid substance can be prepared by adding a surface active substance and the poorly water soluble drug to an aqueous carrier and then mixing at high shear, for example for up to 30 minutes at a shear rate of up to 10,000 rpm. As an example, an admixture of fenofibrate and a phospholipid substance can be prepared by adding a phospholipid substance and fenofibrate to an aqueous carrier and then mixing at high shear for up to 30 minutes at a shear rate of up to 10,000 rpm. Preferably the drug used to form the admixture is in the form of a powder or small crystals or small pieces that are less than about 5 mm in diameter to facilitate mixing. Larger sized crystals or masses of drug can be milled to about 5 mm or smaller before forming the admixture used in this invention to facilitate mixing.

Suitable aqueous carriers include water, sterile water, water for injection, and buffered water such as phosphate buffered water. The pH of the buffer can be in the range of from 4 to 10, preferably from 7 to 9, and most preferably from 7.5 to 8.5. A preferred aqueous carrier is 0.01 to 10 mM sodium phosphate buffer. The pH of the carrier is preferably established at room temperature before mixing with the phospholipid substance and the poorly water soluble drug and before heating to a first temperature. The pH may be adjusted by addition of an acid or base such as HCl or NaOH to a solution of a phosphate salt. Preferably the aqueous carrier contains no dissolved oxygen.

In one aspect, the aqueous carrier can initially be at a temperature between about 1° C. to about 100° C., preferably between 20° C. and 90° C., and more preferably between 20° C. and 50° C. This is particularly useful for fenofibrate. The aqueous carrier can be heated to the desired first temperature range before or after the addition of the admixture.

In another aspect, the aqueous carrier can be heated to a temperature higher than 100° C., for example superheated up to 275° C. In this case, the aqueous carrier can be contained in a closed vessel or apparatus at a pressure higher than ambient pressure. The superheated aqueous carrier and the admixture can be contained in a pressurized closed system such as a stainless steel vessel or bomb in which high speed shear can be applied. The vessel is preferably connected through suitable piping and valves to a heated homogenization apparatus which further comprises a reservoir and optionally a return pipe that can carry homogenate from the homogenizer back to the vessel if used in a continuous or batch-wise mode. The vapor pressure of water at 100° C. is approximately 14.7 psi and it rises as the temperature is increased. For example, at 120° C. the vapor pressure of water is approximately 28.8 psi; at 140° C. it is approximately 52.4 psi; at 160° C. it is approximately 89.6 psi; at 180° C. it is approximately 145.4 psi; at 200° C. it is approximately 225.5 psi; at 220° C. it is approximately 337 psi; at 240° C. it is approximately 486 psi; at 260° C. it is approximately 680 psi; and at 275° C. it is approximately 863 psi. A closed system useful in this invention can safely contain the heated components of this invention at least at these and higher pressures and temperatures and used to provide small particles of poorly water soluble drug according to this invention.

After the poorly water soluble drug, a surface active substance such as fenofibrate and a phospholipid substance are added to the aqueous carrier, the admixture can then be heated if not already so, preferably in the absence of oxygen such as under a nitrogen or argon atmosphere, until the temperature rises to a first temperature range that is at or above the melting point of the drug. In the case of fenofibrate the admixture in the aqueous carrier can be heated to between 79° C. (the reported lowest melting point of fenofibrate) and 99° C., preferably between 79° C. and 95° C., and most preferably between 80° C. and 90° C. In general it is preferred that the temperature is at or up to about 20° C. above the melting point of the drug. Thus, the preferred first temperature range is in general from the melting point of the drug to about 20° C. above the melting point of the drug. The aqueous carrier can be heated to the first temperature range before or after the addition of the drug and the surface active substance. The admixture is maintained at the first temperature range while high shear mixing is applied. The admixture when thus prepared comprises a crude emulsion of melted drug and surface active substance in the heated aqueous carrier.

During the heating of the admixture, high shear mixing is applied. Suitable shear is derived for example from propeller-containing mixers, homogenizers, blenders, sonicators or other devices capable of producing a heated suspension. Suitable shear rates can range between 500 to 10,000 rpm, preferably 2,000 to 5,000 rpm. High shear mixing can be continued for up to 30 minutes or even longer if needed to form a heated suspension containing the drug. High shear mixing of the admixture when the temperature is below the melting point of the drug provides a suspension of the admixture in the aqueous carrier, and such suspension is useful as an antecedent to the heated suspension that is produced when the temperature is increased to or above the melting point of the drug. Continued application of high shear mixing or application of more vigorous or ultra-high shear mixing when the temperature is above the melting point of the drug can produce a heated homogenate of the admixture in the aqueous carrier. When the temperature is above the melting point of the drug, the heated suspension is a suspension of melted drug and surface active substance in the aqueous carrier. In one aspect, the heated suspension is an emulsion of melted drug and surface active substance in the aqueous carrier. High shear mixing and ultra-high shear mixing can be produced by the input of mechanical energy for example using a mechanical mixer or stirrer or mill configured with a mixing blade or propeller that can induce efficient mixing and particle size reduction through high shear turbulence, turbulent eddies, transfer of high fluid kinetic energy, high energy dissipation, pressure induced cavitation, and similar known mechanisms of homogenization.

In one aspect, devices useful in the preparation of a heated suspension of this invention can be employed in the preparation of the heated homogenate of this invention if sufficient energy is transferred to the particles of the heated suspension to produce a heated homogenate. In this case, heating of the admixture to form a heated suspension and then homogenization of the heated suspension to form a heated homogenate can be done as a continuous step combining step (a) and step (b) into a single step wherein a heated suspension is formed and then converted into a heated homogenate with out substantial change in apparatus or without substantial increase in energy applied to the heated admixture formulation.

As used herein, homogenization refers to the creation of a homogenate or uniform distribution of small particles containing drug in an aqueous carrier as a result of an energetic process being applied to an antecedent composition such as a mixture, admixture, blend, emulsion, suspension, dispersion or other composition of solids or solid particles or liquids or liquid particles or droplets comprising drug and one or more than one surface active substance in an aqueous carrier wherein the homogenate and the small particles produced are at least transiently stable toward phase separation into larger particles or droplets or non-uniform solid or liquid domains. Homogenization, particularly with respect to the formation of a heated suspension and a heated homogenate, can be achieved by input of mechanical energy such as by high shear mixing, ultra high shear mixing, high speed blending, microfluidization, and milling such as by dispersion milling, ball milling, attritor milling, vibrator milling, and media milling, or by application of sonic energy in the form of sonication. Preferably in the case of a mill being used in this process wherein the mill contains media or grinding media, such media is removed in a filtration or other suitable separation process to provide homogenized compositions of this invention. Homogenization is preferably achieved by passing an antecedent composition under high pressure, for example under more than 1000 psi, through a tiny orifice which can result in a decrease in the average diameter and an increase in the number and surface area of particles or droplets in the antecedent composition and produce small particles. A preferred homogenization method comprises passing an antecedent composition under high pressure through a tiny orifice and includes microfluidization, particularly with respect to homogenization to prepare a cooled dispersion of this invention.

The drug can be added to the aqueous carrier as a solid. Preferably for example the drug such as fenofibrate can be added in the form of particles ranging in size up to about 10 mm such as milled or micronized particles or powders. Milled particles can be obtained for example by air jet milling of bulk powdered or crystalline fenofibrate. The drug can also be added to the aqueous carrier as a molten material, i.e., heated at or above its melting point, preferably at the melting point of the drug to about 20° C. above the melting point of the drug but at a temperature less than its decomposition point. For fenofibrate the preferred temperature can be from about 80° C., the melting point of the drug, to about 100° C. although temperatures up to the decomposition point of the drug are also suitable.

The concentration of the surface active substance in the aqueous carrier can vary between 0.1% w/w and 90% w/w, preferably between 0.1% w/w and 50% w/w, and more preferably between 0.2% and 20%, and most preferably between 0.5% to 10% w/w. The concentration of the drug such as fenofibrate in the aqueous carrier can vary between 0.1% w/w and 90% w/w, preferably between 0.5% w/w and 50% w/w, and more preferably between 1% and 20% w/w. For example, in one aspect a currently preferred composition comprises 3% to 10% of a phospholipid substance as a surface active substance and 10% of the poorly water soluble drug fenofibrate in 10 mM phosphate buffer at pH 8 as an aqueous carrier.

The surface active substance can be added to the aqueous carrier at any temperature below its decomposition point. When used as a mixture of surface active substances, the individual components can be added separately to the aqueous carrier or combined as mixtures before addition. The surface active substance can be added together with the drug, for example with fenofibrate or separately to the aqueous carrier.

The admixture of the drug, for example fenofibrate, and a surface active substance such as a phospholipid substance in an aqueous carrier is heated to a first temperature range during the application of a high shear mixing to produce a heated suspension containing the drug.

The heated suspension containing the drug is then homogenized at the first temperature range to form a heated homogenate. The first temperature range is maintained during this homogenization to ensure that the drug is maintained in a molten state. For fenofibrate, the first temperature range is preferably from 79° C. to 100° C. and more preferably from 80° C. to 100° C. provided that fenofibrate remains molten.

Homogenization of the heated suspension containing the drug can be carried out in equipment suitable for that process. Useful equipment includes commercially available high pressure homogenization equipment such as APV Gaulin M15, Avestin Emulsiflex C5 or C50, and MFIC Microfluidizer M110EH and other microfluidizers heated to the first temperature range, for example by use of electrical resistance, heated air bath, or heated fluid bath such as a water or silicone oil bath heated to the first temperature range that is at or above the melting point of the drug.

Homogenization of the heated suspension containing the drug is done at a first pressure range in the homogenization chamber of a heated homogenization apparatus while the drug is maintained in its molten state. The first pressure range can be from 2,000 psi to 30,000 psi, preferably about 5,000 psi to 20,000 psi, and more preferably from about 3,000 psi to about 10,000 psi.

The heated suspension containing the drug can be processed into the homogenization chamber of the homogenization apparatus by gravity feed from a heated and optionally stirred reservoir or by aid of a pump, for example a peristaltic pump, from a reservoir heated to the first temperature range through the heated homogenization chamber of the heated homogenizer and thence into a heated receiving vessel heated to the first temperature range in such a manner as to ensure the entire fluid volume of the heated suspension is subjected to discrete homogenization resulting in a homogeneous suspension of heated submicron or micron molten particles. In one aspect of this invention, between each homogenization pass the processed heated suspension is returned batch-wise from the heated receiving vessel back into the heated reservoir such as by means of a pump or by pouring, and the heated homogenization step is repeated. In another aspect, the processed heated suspension is fed directly back into the heated reservoir in a continuous process. If the aqueous carrier is heated above 100° C., the system is contained as a closed system under pressure during the feeding of the admixture to the homogenization apparatus and during the return of the homogenized or partially or not-completely homogenized heated suspension to the heated reservoir. If the initial volume of the heated suspension before homogenization is defined as a volume pass, then the number of volume passes made through the homogenizer in this manner can range from one to about 20, preferably from one to ten, more preferably from 2 to 8, and most preferably from 4 to 7 to produce a heated homogenate that is initially at the first temperature range at or above the melting point of the drug. A preferred drug in this process is fenofibrate which has a preferred first temperature range of from 80° C. to about 95° C.

We have found that this heated homogenate can be cooled to a transiently stable or metastable cooled homogenate. By metastable we mean that upon agitation or long-term standing the transiently stable particles of the cooled homogenate will convert to larger particles of crystallized or precipitated drug and can demonstrate phase separation of components of the homogenate from the aqueous carrier. For example, under these conditions fenofibrate forms a transiently stable or metastable cooled homogenate that on standing or application of manual agitation such as shaking or stirring produces larger crystals. However, we have surprisingly found that the lifetime of the transiently stable particles of the cooled homogenate can be moderately extended by control of cooling conditions. Additional prolonged stability of the small particles can be obtained by subsequent homogenization at a second temperature range that is below the melting point of the drug. We have also found that the total number of homogenization volume passes used in the heated and cooled homogenization processes of this invention is substantially fewer than the number of volume passes needed to produce a comparable drug suspension starting from the powdered or micronized drug that was used to prepare the admixture in this invention but homogenized while the drug was maintained entirely in the solid state according to prior art methods.

In one aspect, particle size of the heated homogenate can be measured using a laser light diffraction based instrument such as a Malvern Mastersizer Microplus and shown to be less than one micrometer.

If an attempt is made to collect the heated homogenate in a receiving vessel that is not preheated to the first temperature, a poorly water soluble drug such as fenofibrate immediately precipitates from the heated homogenate as a solid, and in the case of fenofibrate as crystals. This is very likely related to agitation of the transiently stable dispersion.

In the case of fenofibrate, microscopic examination of a heated homogenate shows it to be comprised of small and non-crystalline particles in suspension, but there is a tendency for fenofibrate to crystallize out on the microscope slide. This rapid crystallization is also seen if the heated homogenate is collected in a receiver at ambient temperature.

A transiently stable or metastable cooled homogenate can be obtained from a heated homogenate derived from an admixture of drug and a surface active substance such as a phospholipid substance in an aqueous carrier by rapidly cooling the heated homogenate under non-agitating conditions from a first temperature range at or above the melting temperature of the drug to a second temperature range below the melting point of the drug, preferably to the range of 1° C. to about 20° C. In some cases, depending on how readily the drug crystallizes, under non-stirred conditions the cooled homogenate can retain small non-crystalline particles very similar to those detected initially in the heated homogenate. Optionally, the heated homogenate can be held at the first temperature range that is above the melting point of the drug, for a holding time before the onset of cooling to the second temperature range. Agitation during the holding period above the melting point of the drug does not effect crystallization of the drug. However, agitation such as by stirring of the cooled homogenate can induce growth in particle size and crystallization and precipitation of drug.

In particular, in the case of fenofibrate we have found that a transiently stable or metastable cooled homogenate can be obtained from a heated homogenate derived from an admixture of fenofibrate and a phospholipid substance in an aqueous carrier by rapidly cooling the heated homogenate under non-agitating conditions from a first temperature range at or above the melting temperature of fenofibrate to a second temperature range below the melting point of fenofibrate, preferably to the range of 1° C. to about 20° C. Under non-stirred conditions the cooled homogenate retains small non-crystalline particles very similar to those detected initially in the heated homogenate. Optionally, the heated homogenate can be held at the first temperature range, for example at 80° C. to 90° C., for a holding time before the onset of cooling to the second temperature range. Agitation during the holding period does not effect crystallization of the fenofibrate.

To determine a minimum holding time at 80 to 90° C. before the induction of cooling for a fenofibrate-containing heated homogenate, the holding time was varied at 15 minute intervals from 0 to 60 minutes and a cooling period in a bath held at 5° C. was kept constant at 30 minutes after the onset of cooling. In these experiments we find that particle mean diameters of the cooled homogenate are similar under all conditions studied. Thus, samples of freshly prepared heated homogenate can be held at a first temperature range for a holding period or they can be immediately cooled to a second temperature range after completion of the first homogenization step.

A number of cooling methods can be applied to the heated homogenate containing a poorly water soluble drug to cool it from the first temperature range at or above the melting point of the drug to a temperature below the melting point of the drug to form a cooled homogenate. Examples of several methods are listed and illustrated with respect to fenofibrate as follows.

Method 1: slow cooling in ambient air optionally in a closed vessel that excludes oxygen and air by allowing the heated homogenate to stand unagitated and to cool from above the melting point of the drug to ambient room temperature;

Method 2: slow unagitated cooling from above the melting point of the drug which for fenofibrate is about 85° C. in a water bath at ambient temperature which is approximately 15° C. to 2° C.;

Method 3: slow stepwise cooling at 1 degree Centigrade per minute in a stirred oil bath from above the melting point of the drug to ambient temperature;

Method 4: slow stepwise cooling from above the melting point of the drug to about 20° C. below the melting point of the drug which for fenofibrate is from about 85° C. down to 65° C., followed by cooling to 4° C. in an isothermally cooled 4° C. water bath;

Method 5: fast cooling in an isothermally cooled 4° C. water bath;

Method 6: slow stepwise cooling from above the melting point of the drug to about 40° C. below the melting point of the drug which for fenofibrate is from about 85° C. to about 40° C. at the rate of 1 Centigrade degree per minute.

For cooling from temperatures initially above 100° C. the heated homogenate is maintained in a pressurized vessel. After cooling, the pressure can then be optionally adjusted to ambient without agitation of the contents of the vessel typically by means of a valve that permits pressure equalization to ambient pressure conditions. Preferably an inert atmosphere such as a nitrogen or argon atmosphere is maintained in contact with the formulations of this invention.

The effect of stirring during the cooling phase was examined for fenofibrate as an example. In some studies, samples were left unagitated while others were stirred magnetically at 250 rpm using Teflon-coated magnetic stirring bars during cooling methods. Additionally, in some experiments, heated homogenate was diluted ten fold with additional aqueous carrier that had been heated to the first temperature, the diluted heated homogenate was then swirled to evenly distribute the added aqueous carrier, and then the diluted heated homooenate was cooled.

Particle size determinations were carried out using a Malvern Microplus Mastersizer. Samples were examined at two to three hours after the initiation of cooling. Results are reported as volume weighted averages or D(4,3). Samples were also examined microscopically under bright polarized light using both in-phase and out-of-phase modes. In-phase light allowed determination of the primary particle size and the detection of aggregates. Out-of-phase examination gave an indication of the amount of crystals formed in the composition. Morphologically small crystalline particles of fenofibrate were easily distinguished from large fenofibrate crystals.

When 3% LIPOID E80 (also sometimes referred to as E80 herein below) was used as a phospholipid substance in a single pass homogenization preparation of a heated homogenate containing 10% fenofibrate, little difference was observed in the particle characteristics when cooled by either method 1 or 2 (average particle size at 3 hours was 2.42 and 2.96 micrometers, respectively). The particles were initially non-crystalline, spherical and submicron but crystals appeared within 3 hours. In contrast, when 3% LIPOID E80 was used as a phospholipid substance in a two pass homogenization preparation of a heated homogenate containing 10% fenofibrate, a smaller particle size was unexpectedly observed when a sample was cooled by method 1 versus when a sample was cooled by method 2 (0.56 and 1.64 micrometers, respectively after 3 hours of cooling). This difference was different from that seen in heated homogenates prepared with saturated lipids such as PHOSPHOLIPON 100H (also sometimes referred to as 100H herein below) and PHOSPHOLIPON 90H (also sometimes referred to as 90H herein below) when processed for two passes. In these formulations, the particle size at 2 to 3 hours after initiation of cooling was significantly higher than that seen using LIPOID E80. For heated homogenates prepared using 3% PHOSPHOLIPON 100H in two passes and cooled for 3 hours according to methods 1 and 2, the average particle sizes were 14.72 and 10.31 micrometers, respectively. For heated homogenates prepared using 3% PHOSPHOLIPON 90H in two passes and cooled for 2 hours according to methods 1 and 2, the average particle sizes were 6.07 and 5.23 micrometers, respectively. Microscopically the cooled homogenates containing PHOSPHOLIPON 100H and PHOSPHOLIPON 90H consisted of particle aggregates with crystals appearing over time. Aggregates were not typically seen in LIPOID E80 formulations but crystal growth occurred over time.

It was unexpectedly found that increasing the cooling rate in the absence of agitation produced cooled homogenates that maintained small particles containing the poorly water soluble drug fenofibrate to a greater degree than those produced by slow cooling methods. This was especially true when LIPOID E80 was used as the phospholipid substance. For example, when a sample of heated homogenate prepared from 3% LIPOID E80 as the surface active substance and 10% fenofibrate in two homogenization passes was cooled by method 5 (fast cooling) and compared to a cooled sample of heated homogenate of the same composition cooled according to methods 1 or 2 (slow cooling), the particle size at 3 hours for fast cooling was 0.63 micrometers versus 0.76 micrometers for slow cooling.

For non-stirred samples, minimal particle size increases can be observed in all cooling methods while under stirred conditions substantial crystallization or precipitation or agglomeration of poorly water soluble drug can be observed. For example, for non-stirred samples containing fenofibrate, minimal particle size increases were observed in all cooling methods. In contrast, under stirred conditions substantial crystallization of fenofibrate was observed for all cooling methods. For samples cooled in a slow step process, crystal growth occurred at temperatures lower than about 20° C. below the melting point of the drug, i.e., for fenofibrate below about 60° C.

It can be seen that energy imparted to the cooled homogenate by mechanical stirring for example using a stirring bar or spatula is not sufficient to impart stability to the particles of the cooled homogenate. To be effective, a particle stabilizing energetic process must impart sufficient energy to the particles of the cooled homogenate to convert them from a transiently stable homogenate into a longer lived dispersion of particles. Otherwise, undesirably large particles will be produced from the transiently stable cooled homogenate. Preferred particle stabilizing energetic processes include sonication and homogenization. A most preferred particle stabilizing energetic process is homogenization. It is believed that enough energy must be applied to the particles to modify some aspect of the particle composition which, while currently unknown, may be related to further reduction in particle size in the presence of a surface active substance or reorganization of drug and/or surface active substance molecules at or on the surface of the particle, or other phenomena.

Diluting the heated homogenate ten fold with additional heated aqueous carrier was found unexpectedly to have a beneficial effect on the size of particles when cooled. Results for fenofibrate as an example are displayed in Table 1.

TABLE 1

Effect of dilution with aqueous carrier on cooled particle sizes in micrometers of heated homogenate containing 10% fenofibrate and 3% phospholipid

| Phospholipid (one pass) | E80 | E80 | 100H | 100H | 90H | 90H |
| --- | --- | --- | --- | --- | --- | --- |
| Cooling method (time of cooling) | 1 (3 h) | 2 (3 h) | 1 (3 h) | 2 (3 h) | 1 (2 h) | 2 (2 h) |
| Undiluted average particle size | 2.42 | 2.96 | 11.46 | 9.71 | 4.83 | 4.12 |
| Diluted average particle size | 1.84 | 1.69 | 3.29 | 3.77 | 2.17 | 2.73 |

Cooled homogenate having particle size of less than 1 micrometer can usually be achieved by subjecting the heated homogenate containing melted drug to multiple homogenization passes prior to rapid cooling. The effect of multiple homogenization is to produce smaller particles, but the size reducing effect is non-linear and shows decreasing rates of return, i.e., the average particle size decreases non-linearly with an increasing number of passes.

In the case of fenofibrate, it was also found that increasing the number of heated homogenization passes from one to two followed by cooling produced a cooled homogenate with smaller particle size with LIPOID E80 but not with PHOSPHOLIPON 100H or PHOSPHOLIPON 90H. For example, at 3 hours after cooling, a cooled homogenate sample containing fenofibrate prepared according to method 1 had a particle size of 0.56 micrometers when the antecedent heated homogenate had been subjected to two passes of homogenization compared to a particle size of 2.42 micrometers when the antecedent heated homogenate had been subjected to one homogenization pass. When a heated homogenate had been subjected to 10 homogenization passes, the cooled homogenate had a particle size of 0.29 micrometers. It was generally found that cooled homogenate having particle size of about 0.3 micrometers could be achieved from heated homogenate that had been subjected to at least 5 homogenization passes. Additional homogenization produced smaller particles, but at decreasing rates per volume pass. For examples, particles as small as 0.05 micrometers can be achieved under homogenization conditions. Results for one and two homogenization volume passes as a function of phospholipid are displayed in Table 2.

TABLE 2

Difference between one and two heated homogenization passes on cooled particle sizes in micrometers of heated homogenates containing 10% fenofibrate and 3% phospholipid

| Phospholipid (no. of pass) | E80 | E80 | 100H | 100H | 90H | 90H |
|---|---|---|---|---|---|---|
| Cooling method (time of cooling) | 1 (3 h) | 2 (3 h) | 1 (3 h) | 2 (3 h) | 1 (2 h) | 2 (2 h) |
| One pass average particle size | 2.42 | 2.96 | 11.46 | 9.71 | 4.83 | 4.12 |
| Two pass average particle size | 0.56 | 1.64 | 14.72 | 10.31 | 6.07 | 5.23 |

We have also found that the pass dependent particle size of the cooled homogenate can be a function of the ratio of the concentration of surface active substance to drug. For example, a heated homogenate prepared using 3% LIPOID E80 as the surface active substance and 10% fenofibrate as the drug and subjected to 10 homogenization passes produced a cooled homogenate by method 6 that had a particle size of 0.35 micrometers while a heated homogenate prepared using 10% LIPOID E80 as the surface active substance and 10% fenofibrate as the drug and subjected to 10 homogenization passes produced a cooled homogenate by method 6 that had a particle size of 1.3 micrometers.

Furthermore, when a heated homogenate was prepared using 3% Phospholipon 100H as the surface active substance and 10% fenofibrate as the drug, subjected to 10 homogenization passes and cooled, a cooled homogenate was produced by method 5 that had a particle size of 1.45 micrometers. In comparison, when a heated homogenate was prepared using 3% LIPOID E80 as the surface active substance and 10% fenofibrate as the drug, subjected to 10 homogenization passes and cooled, a cooled homogenate was produced that had a particle size of 1.3 micrometers.

Fast cooling of heated homogenates in a 4° C. bath under non-stirred conditions produces cooled homogenates with minimum change in morphology and particle size from that observed in the heated homogenates prior to cooling. For example, we have discovered that fast cooling of heated homogenates containing a phospholipid as the surface active substance and fenofibrate as the drug in a 4° C. bath under non-stirred conditions produced non-crystalline cooled homogenates with minimum change in morphology and particle size from that observed in the heated homogenates prior to cooling. When samples of heated homogenate were held at 80° C. for up to one hour and then cooled to form cooled homogenates that were held for 30 minutes at 5° C., no differences in particle size could be detected as a function of the time the heated homogenate was held at 80° C. before cooling. For optimum processing speed, freshly prepared samples of heated homogenate can be cooled from the first temperature range to a second temperature range immediately after an adequate number of homogenization passes such as five passes of heated homogenization to provide cooled homogenates. However, cooled homogenates thus prepared appear to be transiently stable or metastable toward formation of crystals of drug that can grow larger and precipitate from the suspension of the cooled homogenate if allowed to stand. The formation of larger particles and crystals is enhanced if the cooled homogenate is disturbed such as by stirring or shaking.

In another aspect of this invention, bulking agents can be added as solids or in solutions of aqueous carrier to the admixture of drug and a surface active substance in an aqueous carrier in the process of this invention.

A bulking agent is herein defined as a compound useful in assisting redispersion of dried small particles back into a suspension such as an aqueous suspension. Suitable bulking agents include hydroxyl-containing, hydrophilic, relatively low molecular weight (less than 50,000) compounds such as monosaccharides, disaccharides, trisaccharides, sucrose, lactose, mannitol, sorbitol, trehalose, glycerol, dextrose, fructose, sugars, pentoses, hexoses, xylitol, and mixtures thereof. Bulking agents are useful as protectants in a drying process such as cryoprotectants in a lyophilization process or as additives in a spray drying process or an evaporation process, preventing or substantially reducing particle fusion, combination, suspension degradation and agglomeration during drying, and assisting in the resuspension of particles from a dried state. Dry small particles containing a poorly water soluble drug can be produced for example as a lyophilizate which is a solid produced from a cooled dispersion of particles by the process of freezing the aqueous carrier to a solid comprising a dispersion in ice and then removing the water by subliming the ice under reduced pressure. Bulking agents can also reduce or depress the freezing point of aqueous compositions in which they are dissolved or partially dissolved.

Preferred bulking agents include trehalose, sucrose, sorbitol, and mixtures thereof.

Bulking agents can be added to the admixture, to the heated suspension, to the heated homogenate, to the cooled homogenate, to the cooled dispersion, and to the dried particles. They can be added as solids or as liquids or as solutions in aqueous carrier.

The stability of cooled homogenate formulations with respect to the effect of addition of a bulking agent or a combination of bulking agents was examined. When bulking agents were added as solids or liquids to heated admixtures of fenofibrate and a phospholipid substance as a surface active substance in an aqueous carrier, then processed for example using 10 heated homogenization passes at 80° C. and subsequently cooled in a 4° C. water bath, particle size estimates suggested that with the exception of the bulking agent sucrose (10%), there was little increase in particle mean diameter measurements over a 2 h period. However microscopic observations revealed the presence of a significant number of large crystals after the cooling step. Addition of 2-fold hot buffer solution containing either nothing or bulking agents to the processed formulations caused a large increase in the mean particle diameter. This was attributed by microscopic examination to be due to particle aggregation together with large crystals also present.

When trehalose was added to an admixture of fenofibrate and a phospholipid substance in an aqueous carrier, on stirring crystals were detected indicating that trehalose did not stabilise these metastable formulations with respect to crystal formation and precipitation. PVP 17 and glycerol were added to heated homogenates, and in both cases crystal growth was observed microscopically under stirred conditions. When glycerol alone or glycerol and trehalose were added to the admixture and then homogenized, results from stirring experiments again showed that these formulations were unstable with extensive crystallization observed over time. Thus, adding bulking agents or PVP to either the admixture or to the heated homogenate does not result in stabilization of the metastable formulation under stirring conditions.

Whereas a cooled homogenate can be unstable with respect to agitation such as stirring or manual shaking, we have surprisingly found that a cooled homogenate can be transformed into a more stable cooled dispersion by application of a particle stabilizing energetic process applied at the second temperature range and in a second pressure range.

For example, although the aforementioned cooled homogenates of fenofibrate was found to be unstable with respect to agitation such as stirring or manual shaking that lead to the formation of crystals of fenofibrate, we have found that the cooled homogenate can be transformed into a more stable cooled dispersion by application of a particle stabilizing energetic process applied at the second temperature range and in a second pressure range.

Examples of suitable particle stabilizing energetic processes include homogenization, microfluidization, and sonication. Microfluidization is generally considered to be a method of homogenization.

In one aspect, particles of a heated homogenate containing a poorly soluble drug can be non-crystalline while the cooled dispersion particles produced as a result of application of a particle stabilizing energetic process can be crystalline. While stirring can induce significant particle growth in a cooled homogenate, stirring does not induce significant particle growth in a cooled dispersion formed from the cooled homogenate. The cooled dispersion thus produced is more robust toward particle growth than the cooled homogenate. The particles of the cooled dispersion are preferably in the micron and submicron range. Depending on the number of stabilizing processing steps, i.e., volume passes, employed in the preparation of the cooled dispersion, the cooled dispersion can also comprise weakly associated aggregates of particles that can be readily broken up or dispersed or de-aggregated by stirring the dispersion. Preferably, an increase in the number of processing steps from 1 to a range of from 5 to 20, preferably from 10 to 20, can produce fewer and more easily dispersed aggregates. Formulation instability toward stirring can be increased as a result of the particle stabilizing energizing process.

Microscopically, in the case of fenofibrate as an example of a poorly soluble drug, heated homogenate particles are non-crystalline while cooled dispersion particles produced as a result of application of a particle stabilizing energetic process are crystalline. Importantly, while stirring can induce significant particle growth in a cooled homogenate, stirring does not induce significant particle growth in a cooled dispersion formed from the cooled homogenate. The cooled dispersion thus produced is more robust toward particle size growth than the cooled homogenate. One possible explanation is that the number of nucleation sites for formation of crystals of the poorly soluble drug is substantially increased by application of a particle stabilizing energetic process in the presence of a surface active substance giving rise to stable small crystalline particles in the micron and submicron range.

A preferred particle stabilizing energetic process is microfluidization for example using a Microfluidix M110EH apparatus. Microfluidization can be accomplished using from 1 to 20 volume passes, preferably from 2 to 20 volume passes, more preferably from 5 to 20 volume passes, and most preferably from 10 to 20 volume passes. Microfluidization can be done in continuous mode or in batch mode. A preferred second temperature range is the second temperature range used for the preparation of the cooled homogenate and is preferably from 1° C. to 40° C., more preferably from 4° C. to 20° C. and most preferably from 4° C. to 15° C. A useful pressure range for the preparation of the cooled dispersion is a second pressure range, that is, from 2,000 to about 30,000 psi, preferably from 5,000 to about 20,000 psi, and most preferably from 5,000 to 18,000 psi.

Microscopically, in the case of fenofibrate as an example, the cooled dispersion is a suspension of crystalline fenofibrate particles. Depending directly on the number of stabilizing processing steps or volume passes employed in the preparation of the cooled dispersion, the cooled dispersion can also comprise weakly associated aggregates of crystalline fenofibrate particles that can be broken up or dispersed or de-aggregated by stirring the suspension.

A reduction in the cooled dispersion particle mean diameter can be achieved by increasing the number of volume passes during the cold homogenization step. For example, as shown in Table 3 for a formulation derived from an admixture of 3% LIPOID E80 as the surface active substance and 10% fenofibrate as a poorly water soluble drug processed first for 10 volume passes to form a heated homogenate containing the drug, cooled according to method 5 to form a transiently stable cooled homogenate containing the drug, and then microfluidized for 2 volume to 10 volume passes to form a cooled dispersion of small particles containing the drug, the observed mean diameter was 0.26 to 0.54 micrometers as a cooled homogenate prior to undergoing a particle stabilizing energizing process, 1.45 micrometers as a cooled dispersion when processed for 2 volume passes, and 0.9 micrometers when processed for 10 volume passes. Surprisingly, formulation instability toward stirring was dramatically increased as a result of the particle stabilizing energizing process. Without the additional particle stabilizing energizing process, the average particle size of the cooled homogenate increased by two orders of magnitude with stirring within 30 minutes. However, after application of the particle stabilizing energizing process, the average particle size did not increase substantially with stirring up to 24 hours. In addition, the average particle size of the cooled dispersion was smaller and remained smaller up to 5 days when the formulation was processed for 10 volume passes.

TABLE 3

Particle size changes of cooled homogenate and cooled dispersion From an admixture of 10% Fenofibrate, 3% Lipoid E80 as the surface active substance in 10 mM phosphate buffer at pH 8. Keeping temperature was 4° C.

|  | Time (minutes) | Average size not stirred (micrometers) | Average size stirred (micrometers) |
| --- | --- | --- | --- |
| Cooled homogenate (10 volume Passes) | 0 | 0.26 | 0.26 |
|  | 30 | 0.26 | 14.22 |
|  | 60 | 0.54 | 9.44 |
| Cooled dispersion (2 volume Passes) | 0 | 1.45 | 1.45 |
|  | 30 | 1.45 | 1.29 |
|  | 60 | 1.37 | 1.37 |
|  | 1440 | Not measured | 1.12 |
| Cooled dispersion (10 volume passes) | 0 | 0.87 | Not measured |
|  | 1140 | 0.93 | Not measured |
|  | 5700 | 0.97 | Not measured |

When egg lecithin LIPOID E80 was replaced with PHOSPHOLIPON H 100, the cooled homogenate particle size was higher after the 10 passes than with LIPOID E80 equivalent (2.3 micrometers versus 0.3 micrometers, respectively). In addition after processing to form a cooled dispersion of small particles containing the drug, a further relative increase in particle size of cooled dispersion was detected. This can be attributed to aggregation of the primary particles. For both the LIPOID E80 formulation and the PHOSPHOLIPON H 100 formulation, aggregate sizes could be decreased over time with stirring.

Scanning electron microscopic (SEM) analysis of cooled dispersions prepared originally from fenofibrate and a phospholipid as a surface active substance in the admixture and by 10 volume passes revealed them to exist as single crystalline particles each about 1 micron in mean diameter. Cooled dispersions are comparable to microfluidized formulations of phospholipid and fenofibrate that can be prepared by microfluidization below the melting point of fenofibrate such as according to IDD-PTM technology developed by RTP Pharma Inc. as described in U.S. Pat. No. 5,091,187 which is hereby incorporated by reference. However, to achieve such particle size reduction without first melting the drug can require substantially more volume passes of microfluidization, for example as many as 200 passes at ca. 18,000 psi.

In another aspect of this invention, more than one surface active substances can be used to prepare formulations according to this invention. At least one surface active substance is needed to prepare the initial admixture of this invention, and in one aspect can suffice in the preparation of subsequent heated suspensions, heated homogenates, cooled homogenates, cooled dispersions and dried particles prepared according to this invention. In another aspect, addition of more than one surface active substance can be made to the admixture, the heated suspension, the heated homogenate, the cooled homogenate, and the cooled dispersion of this invention. Such additions can be made at one individual step in the process or at more than one step in the process. For example, a second surface active agent can be added to the admixture or to the heated suspension, and additional amounts of the second surface active agent or a third surface active agent can be added to the cooled homogenate or to the cooled suspension or even to the dried small particles prepared according to this invention.

The total concentration of one or of more than one surface active substance added to the formulations prepared according to this invention can be in the range of 0.1 to 50%, preferably 0.2 to 20%, and more preferably 0.5 to 10%.

In another aspect of this invention, bulking agents can be added to the admixture, to the heated homogenate, to the cooled homogenate, and to the cooled dispersion. Bulking agents can be added as solids, as mixtures, as solutions in aqueous carrier, and in combinations of solids and solutions. Bulking agents can be added at the beginning or end of the steps leading to the formation of a heated homogenate, cooled homogenate, and cooled dispersion, and they can be added at more than one stage during the process. The amount of total bulking agents that can be added ranges from about 0.1% to about 50%, preferably from 1% to about 25%, and more preferably from about 2% to about 20%. Bulking agents can be added as individual agents at these levels or in combination such that the total amount of bulking agent resides within these levels.

Addition of a variety of bulking agents at different steps in the process of this invention does not produce a substantial increase in the mean particle diameter of a cooled dispersion over a period of time such as over 24 hours. For example, when bulking agents sorbitol (5%) and sucrose (10%) were added to a 3% LIPOID E80 and 10% fenofibrate admixture and the formulation was processed for 10 passes to form a cooled homogenate and for 10 passes to form a cooled dispersion of small particles containing the drug, the particle size of the cooled dispersion (0.97 micrometers) was very similar in size to that of an analogous formulation composition (i.e., 0.91 micron) where the same bulking agents were added after the formation of the cooled dispersion.

Homogenization of the cooled homogenate containing the drug can be carried out in equipment suitable for that process. Useful equipment includes but is not limited to commercially available high pressure homogenization equipment such as APV Gaulin M15, Avestin Emulsiflex C5 or C50, MFIC Microfluidizer M110EH, and other microfluidizers and homogenizers. Homogenization can also be carried out using high shear and ultra high shear mechanical mixers and mills and propeller-containing mixers than can impart sufficient turbulence or energy transfer to the particles to form stable small particles. The apparatus is cooled to maintain the cooled homogenate and cooled dispersion at the second temperature range. Cooling can be done by use of a cooled air bath, a cooled fluid bath such as a water or ice/water bath, or a suitable heat exchanger that is cooled and maintained at or below the second temperature range that is below the melting point of the drug.

In a final step of the process, the cooled dispersion can be dried to provide dry small particles containing the poorly soluble drug. Drying can be done using a number of commonly known methods, for example by spray drying, lyophilization, and evaporation. Preferably one or more than one bulking agent is present in the formulation undergoing drying.

When drying is done by spray drying the cooled dispersion is feed into the spray dryer as a liquid, preferably at a temperature in the second temperature range and preferably as a dispersion comprising one or more than one bulking agent.

When drying is done by evaporation, the aqueous carrier of the cooled dispersion can be maintained as a liquid and water is removed under reduced pressure and with application of enough heat to keep at least some and preferably all of the aqueous carrier in the cooled dispersion that is drying in the liquid state until it is dried.

When drying is done by lyophilization, the aqueous carrier of the cooled dispersion is frozen and lyophilized under reduced pressure and application of heat to the frozen suspension to provide a lyophilizate comprising small particles containing poorly soluble drug. Freezing and lyophilization are preferably done in a conventional freeze dryer, for example, in a Virtis Corporation Unitop freeze dryer using conventional techniques. Lyophilization can be done on cooled dispersions added to trays or on cooled dispersions added to vials, for example in 2 mL or 10 mL vials. Bulking agents can be added to the formulation to facilitate reconstitution of the lyophilizate.

In the case of fenofibrate as an example, in a final step of the process, the cooled dispersion can be dried by freezing the aqueous carrier in the dispersion and lyophilizating the frozen dispersion under reduced pressure and by application of heat to provide a lyophilizate comprising small particles containing fenofibrate. Optionally, the cooled suspension can be spray dried to provide a dried powder of particles containing fenofibrate. Alternatively, the water in aqueous carrier of the cooled dispersion can be evaporated, for example under reduced pressure to provide dried small particles containing fenofibrate.

By small particles containing a poorly water soluble drug is meant particles in the range of 0.1 micron to 20 micrometers in average diameter containing a poorly water soluble drug, preferably in the range of 0.1 to 5 micrometers containing a poorly water soluble drug, and most preferably in the range of 0.1 to 2 micron containing a poorly water soluble drug.

By small particles containing fenofibrate is meant particles in the range of 0.1 micron to 20 micrometers in average diameter containing fenofibrate, preferably in the range of 0.1 to 5 micrometers containing fenofibrate, and most preferably in the range of 0.1 to 2 micron containing fenofibrate.

Addition of bulking agents such as sucrose and sorbitol either to the admixture before processing or to the cooled dispersion just prior to drying provides particle size suspensions on reconstitution similar in size to those of the antecedent cooled dispersion. Drying can be done by spray drying or preferably by lyophilization.

Addition of bulking agent such as trehalose either to the admixture before processing, to the heated homogenate, to the cooled homogenate, or to the cooled dispersion just prior to drying provides particle size suspensions on reconstitution that are similar in size to those of the antecedent cooled dispersion.

Samples of cooled homogenate can be dried for example by lyophilization with bulking agents and reconstituted in modified simulated gastric fluid (SGF) with gentle inversion immediately after lyophilization. The particle sizes of the dispersions on reconstitution can be similar to, i.e., the same or slightly larger than, those of the antecedent cooled homogenates. Microscopically, the reconstituted suspensions can exist primarily as single crystalline particles together with occasional aggregates. For example, a cooled dispersion prepared from an admixture of 3% LIPOID E80 as the surface active substance, 10% fenofibrate, 10% sucrose, and 5% sorbitol as an antecedent cooled dispersion has an average particle size of 0.96 micrometers. On reconstitution of the corresponding lyophilizate, the average particle size of the reconstituted suspension is 1.57 micrometers. For the compositionally equivalent formulation where the bulking agents are added to the cooled dispersion, mean particle diameters before and after lyophilization are 0.91 and 1.38 micrometers, respectively.

Other bulking agents, for example glycerol at 2%, sucrose at 5%, also yield dried particles that reconstitute easily and provide suspensions of single crystalline particles.

The period of stability of the particles of the cooled dispersion of stabilized small particles containing the drug can extend from the stability period of the transiently stable particles of the cooled homogenate up to several months. Stability of more than a year is also contemplated.

Formulations prepared by this invention may be dried into powders, which can be resuspended or filled into capsules or converted into granules or tablets with the addition of binders and other excipients known in the art of tablet making. Particles of drug provided according to this invention have bioavailability comparable to or better than similar sized particles prepared by alternate methods.

The invention is additionally illustrated in connection with the following examples, which are considered to be illustrative of the present invention. It should be understood, however, that the invention is not limited to the specific details of the Examples.

The invention is additionally illustrated in connection with the following examples, which are considered to be illustrative of the present invention. It should be understood, however, that the invention is not limited to the specific details of the Examples.

EXAMPLE 1

A mixture of 60 parts of LIPOID E80 as the surface active substance and 200 parts of a poorly water soluble drug, fenofibrate, is homogeneously dispersed in 1440 parts of 10 mM pH 8.0+/−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y operated at 3,400 to 3,600 psig while maintained at 85° C. to 99° C. to form a heated homogenate containing the drug. After 10 passes, the heated homogenate is cooled by passage through a heat exchanger cooled by chilled water at 5° C. to 10° C. and the transiently stable cooled homogenate is further homogenized for 10 to 20 batch volume cycles or passes using a Microfluidics M110 EH homogenizer operated at 18,000 psig (peak) while maintained at 4° C. to 13° C. The resulting cooled dispersion comprising small particles containing fenofibrate of size less than 2.0 microns in diameter is then dried by freezing to about −40° C. and lyophilization under vacuum to produce dried small particles containing fenofibrate.

EXAMPLE 2

A mixture of 60 parts of LIPOID E80 as the surface active substance and 200 parts of a poorly water soluble drug, fenofibrate, is homogeneously dispersed in 1440 parts of 10 mM pH 8.0+/−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y operated at 3,400 to 3,600 psig while maintained at 80° C. to form a heated homogenate containing the drug. After 10 passes, the heated homogenate is cooled by passage through a heat exchanger chilled with ice water, kept at 4° C. for 30 min, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing the drug are of a size less than 1.0 micron in diameter and are then dried by freezing and lyophilization under vacuum to produce dried small particles containing fenofibrate.

EXAMPLE 3

A mixture of 60 parts of LIPOID E80 as the surface active substance and 200 parts of a poorly water soluble drug, fenofibrate, is homogeneously dispersed in 1440 parts of 10 mM pH 8.0 +/−0.2 aqueous phosphate buffer containing 240 parts of trehalose using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to 95° C. to form a heated homogenate containing the drug. After 10 passes, the heated homogenate is cooled by passage through a heat exchanger chilled with ice water, kept at 4° C. for 30 minutes in an ice/water bath, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing drug of size less than 1.0 micron in diameter is then dried by freezing in liquid nitrogen and lyophilization under vacuum to produce dried small particles containing fenofibrate.

EXAMPLE 4

A mixture of 60 parts of LIPOID E80 as the surface active substance and 200 parts of a poorly water soluble drug, fenofibrate, is homogeneously dispersed in 1440 parts of 10 mM pH 8.0+/−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to form a heated homogenate containing drug. After 10 passes, the heated homogenate is cooled by passage through a heat exchanger chilled with ice water, kept at 4° C. for 30 mm, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing the drug of size less than 1.0 micron in diameter is treated with a solution of 200 parts of sucrose plus 100 parts of sorbitol as bulking agents in additional aqueous carrier and is then dried by freezing in liquid nitrogen and lyophilization under vacuum to produce dried small particles containing fenofibrate.

EXAMPLE 5

A mixture of 60 parts of LIPOID E80 as the surface active substance and 200 parts of a poorly water soluble drug, fenofibrate, is homogeneously dispersed in 1440 parts of 10 mM pH 8.0+/−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to form a heated homogenate containing drug. After 10 passes, the heated homogenate is cooled by passage through a heat exchanger chilled with ice water, kept at 4° C. for 30 mm, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing the drug of size less than 1.0 micron in diameter is treated with a solution of bulking agents equivalent to 300 parts of sucrose plus 100 parts of sorbitol in additional aqueous carrier is then dried by freezing and lyophilization to produce dried small particles containing fenofibrate.

EXAMPLE 6

A mixture of 60 parts of LIPOID E80 as the surface active substance and 200 parts of a poorly water soluble drug, fenofibrate, is homogeneously dispersed in 1440 parts of 10 mM pH 8.0+/−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to form a heated homogenate containing drug. After 10 passes, the heated homogenate is cooled by passage through a heat exchanger chilled with ice water, kept at 4° C. for 30 mm, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing drug of size less than 1.0 micron in diameter is treated with 100 parts of sucrose plus 20 parts of glycerol as bulking agents, then dried to produce dried small particles containing fenofibrate.

EXAMPLE 7

A mixture of 60 parts of LIPOID E80 as the surface active substance and 200 parts of a poorly water soluble drug, fenofibrate, is homogeneously dispersed in 1440 parts of 10 mM pH 8.0±1−0.2 aqueous phosphate buffer using a Pro-Scientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M 11.0 Y homogenizer operated at 3,400 to 3,600 psig while maintained at 85° C. to form a heated homogenate containing drug. After 10 passes, the heated homogenate is cooled by passage through a heat exchanger chilled with ice water, kept at 4° C. for 30 mm, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing drug of size less than 1.0 micron in diameter is treated with a cooled solution of 200 parts of trehalose plus 100 parts of PVP 17 as bulking agents in additional aqueous carrier and then dried by freezing and lyophilization or by spray drying to produce dried small particles containing fenofibrate.

EXAMPLE 8

A mixture of 60 parts of LIPOID E80 as the surface active substance and 200 parts of a poorly water soluble drug, fenofibrate, is homogeneously dispersed in 1440 parts of 10 mM pH 8.0+/−0.2 aqueous phosphate buffer containing 200 parts of sucrose and 100 parts of sorbitol using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 80° C. to form a heated homogenate containing drug. After 10 passes, the heated homogenate is cooled by passage through a heat exchanger chilled with ice water, kept at 4° C. for 30 min, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles of size less than 1.0 micrometers in diameter is then dried to produce dried small particles containing fenofibrate.

EXAMPLE 9

An admixture of a formulation comprising 60 parts of a hydrogenated soybean phosphatidylcholine (i.e., PHOSPHOLIPON 100H) as a surface active substance and 200 parts of a poorly water soluble drug, fenofibrate, in 1400 parts of aqueous carrier (10 mM phosphate buffer at pH 8) is heated to 85° C. and homogenized for 10 volume passes to form a heated homogenate containing drug containing the drug, cooled to room temperature according to method 1 to form a transiently stable cooled homogenate containing the drug, and then sonicated for 1 minute using a 550 Sonic Dismembrator Probe Sonicator from Fisher Scientific (10 s pulses at power level 5) to form a cooled dispersion. The mean particle diameter of the sonic ated material (cooled dispersion) is only slightly larger than that of the heated homogenate material, both being between 2–4 micrometers. Microscopically, the heated homogenate particles are non-crystalline while the cooled dispersion particles are crystalline. Importantly, while stirring induces significant particle growth in the cooled homogenate, stirring does not induce significant particle growth in the cooled dispersion. The cooled dispersion thus produced is more robust toward particle growth than the cooled homogenate.

EXAMPLE 10

A mixture of 60 parts of a phospholipid as a surface active substance and 200 parts of a poorly water soluble drug is homogeneously dispersed in 1440 parts of 10 MM pH 8.0+/−0.2 aqueous phosphate buffer using a ProScientific 400 high shear mixer at 2,000 to 3,600 rpm at ambient temperature for 30 minutes, and then heated above the melting point of the drug during continuous high shear mixing at 2,500 to 4,000 rpm. The heated suspension is then recirculatively homogenized for 10 batch volume cycles or passes using a Microfluidizer M110Y operated at 3,400 to 3,600 psig while maintained above the melting point of the drug to form a heated homogenate containing drug. After 10 passes, the heated homogenate is cooled by passage through a heat exchanger chilled with ice water, and the transiently stable cooled homogenate is further homogenized for 10 to 20 batch volume cycles or passes using a Microfluidics M110 EH homogenizer operated at 18,000 psig (peak) while maintained at 4° C. to 15° C. The resulting cooled dispersion comprising particles containing the poorly water soluble drug is then dried by freezing and lyophilization to produce dried small particles containing the poorly water soluble drug.

EXAMPLE 11

Cooled dispersions prepared according to examples 1 to 9 are placed into 10 ml vials and individually frozen and lyophilized to provide dried small particles containing fenofibrate.

EXAMPLE 12

Cooled dispersions prepared according to examples 1 to 9 are individually spray dried to provide dried small particles containing fenofibrate.

EXAMPLE 13

A cooled dispersion prepared according to example 10 using fenofibrate is placed in 10 ml vials, frozen and lyophilized to provide dried small particles containing fenofibrate.

EXAMPLE 14

A cooled dispersion prepared according to example 10 using fenofibrate is spray dried to provide dried small particles containing fenofibrate.

EXAMPLE 15

A mixture of 225 parts of LIPOID E80 as the surface active substance, 750 parts of fenofibrate, 375 parts of sorbitol, and 750 parts of sucrose is homogeneously dispersed in 6000 parts of 10 mM pH 8.0+/−0.2 aqueous phosphate buffer using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M 110Y operated at 3,400 to 3,600 psig while maintained at 85° C. to 99° C. to form a heated homogenate containing the drug. After 10 passes, the heated homogenate is cooled by passage through a heat exchanger cooled by chilled water at 5° C. to 10° C. and the transiently stable cooled homogenate is further homogenized for 10 to 20 batch volume cycles or passes using a Microfluidics M110 EH homogenizer operated at 18,000 psig (peak) while maintained at 4° C. to 13° C. The resulting cooled dispersion comprising small particles containing fenofibrate of size less than 1.0 micron in diameter is then dried by freezing to about 40° C. and lyophilization under vacuum to produce dried small particles containing fenofibrate.

EXAMPLE 16

The dried small particles containing fenofibrate prepared in Example 15 are blended with 2% Cabosil, 5% sucrose, and 0.25% magnesium stearate. After thorough blending, the mixture is compressed, optionally with an intermediate formation of compressed slugs of the composition which are milled, optionally sieved to a uniform particle size range, and then recompressed into tablets for oral dosing. The tablets are prepared at the following dosage levels of fenofibrate and are sized according to volumes encountered.

50 mg
51 mg
52 mg
53 mg
54 mg
67 mg
100 mg
102 mg
104 mg
106 mg
134 mg
150 mg
153 mg
156 mg
159 mg
160 mg
200 mg
213 mg
250 mg
300 mg

EXAMPLE 17

Gelatin capsules are filled with the dried small particles containing fenofibrate prepared in Example 15 and sealed to provide capsules for oral dosing. The capsules are filled at the following dosage levels of fenofibrate and are sized according to volumes encountered.

50 mg
51 mg
52 mg
53 mg
54 mg
67 mg
100 mg
102 mg 104 mg
106 mg
134 mg
150 mg
153 mg
156 mg
159 mg
160 mg
200 mg
213 mg
250 mg
300 mg

EXAMPLE 18

Oral bioavailability of a microfluidized phospholipid-stabilized microparticle formulation of fenofibrate in human subjects.

An oral capsule dosage form of a formulation of microfluidized PHOSPHOLIPON 100H-stabilized fenofibrate microparticles (67 mg dose of fenofibrate) prepared with TWEEN 80 and mannitol was administered to human volunteers. The study consisted of oral administration of capsules containing a formulation of microfluidized PHOSPHOLIPON 100H-stabilized fenofibrate microparticles to eight human volunteers in a single dose crossover design, using a commercially marketed formulation of micronized fenofibrate as a reference. The dose administered was 67 mg. Blood samples were collected before and after each administration at various time points over 120 hours. The drug concentration in blood samples was determined by high-pressure liquid chromatography by monitoring for the level of the metabolite, fenofibric acid. The pharmacokinetic results are presented in Table 5. The ratio of the least-squares means (ln-transformed data) was 1.49±0.24, and demonstrate the superior bioavailability of fenofibrate in the microfluidized phospholipid-stabilized fenofibrate microparticle formulation over the commercially available product.

TABLE 5

$C_{max}$ and $AUC_{0\text{-}inf}$ for Fenofibric Acid

| | $C_{max}$ (ng.ml$^{-1}$) | $AUC_{0\text{-}\infty}$ (ng.ml$^{-1}$.h) |
|---|---|---|
| Microfluidized phospholipid-stabilized fenofibrate microparticle formulation (67 mg) | 2528 | 57236 |
| Commercially available micronized fenofibrate (67 mg) product | 1372 | 38629 |
| Dunnett's t-test (log-transformed data) | p < 0.05 | p < 0.05 |

EXAMPLE 19

Elimination of the food effect associated with marketed formulations of fenofibrate using a microfluidized phospholipid-stabilized microparticle formulation of fenofibrate in human subjects.

The oral bioavailability of a capsule dosage form of a microfluidized phospholipid-stabilized microparticle formulation of fenofibrate comprising PHOSPHOLIPON 100H-stabilized fenofibrate microparticles prepared by microfluidization, TWEEN 80, and mannitol was tested and compared with the marketed micronized formulation of fenofibrate in fasting and fed states in a single dose pharmacokinetic study. The study consisted of the oral administration of capsules of the test formulations to 8 human subjects in a single dose, crossover design with four treatment periods. Both drug formulations were administered as 67 mg capsules. Blood samples were collected before and after each administration at various time points over 120 hours. The drug concentration in blood samples was determined by high-pressure liquid chromatography by monitoring for the level of the metabolite, fenofibric acid. The bioavailability ($AUC_{0\text{-}\infty}$) under the different conditions is presented in Table 6. The food effect is represented by the ratio of the $AUC_{0\text{-}\infty}$ under fed and fasted conditions. The results demonstrate a significant (p<0.05) food effect with the marketed micronized fenofibrate product (73%), while the food effect with the microfluidized phospholipid stabilized microparticle fenofibrate was only 13% (NS), demonstrating the virtual elimination of the dependence on food for optimal bioavailability.

TABLE 6

$AUC_{0\text{-}\infty}$ for fenofibric acid under fasted and fed conditions

| $AUC_{0\text{-}\infty}$ (ng.ml$^{-1}$.h) | Microfluidized phospholipid stabilized microparticle fenofibrate (67 mg) | Marketed micronized fenofibrate product (67 mg) |
|---|---|---|
| Fasting state | 57236 | 38629 |
| Fed state | 64585 | 66969 |
| $F_{rel}$ (fed/fasted) | 1.13 | 1.73 |
| Dunnett's t-test (ln-transformed data) | NS | p < 0.05 |

EXAMPLE 20

Demonstration of the absence of food effect with a microfluidized phospholipid-stabilized microparticle formulation of fenofibrate (IDD-PT™ fenofibrate) in human subjects.

| Parameters (N = 24) | 160 mg fenofibrate formulation of this invention fed with a low fat meal | | | 200 mg Tricor ® fed with a low fat meal | | |
|---|---|---|---|---|---|---|
| | Mean | +/− SD | CV (%) | Mean | +/− SD | CV (%) |
| $AUC_{0\text{-}t}$ = experimental area under the curve calculated according to the linear trapezoidal rule (ng.h/mL) | 137587.71 | 48203.28 | 35.03 | 149272.07 | 58621.21 | 39.27 |

| -continued | | | | | | |
|---|---|---|---|---|---|---|
| $AUC_{0-\infty}$ = area under the curve extrapolated to the infinite (ng.h/mL) | 140067.57 | 49380.22 | 35.25 | 152599.13 | 60529.39 | 39.67 |
| $C_{max}$ = maximal plasma concentration (ng/mL) | 11204.05 | 2507.73 | 22.38 | 10401.84 | 3039.54 | 29.22 |
| % extrapolated | 1.76 | 1.13 | 63.91 | 2.12 | 1.22 | 57.83 |
| $t_{max}$ = time to reach the maximal plasma concentration (hours, h) | 3.21 | 1.10 | 34.36 | 4.75 | 0.90 | 18.88 |
| $k_{el}$ = elimination rate constant ($h^{-1}$) | 0.0507 | 0.0220 | 43.51 | 0.0449 | 0.0177 | 39.37 |
| $t_{1/2el}$ = half-life of elimination (h) | 15.72 | 5.47 | 34.76 | 17.77 | 6.51 | 36.63 |
| $F_{rel}$ = relative bioavailability (%) | 94.05 | 12.36 | 13.14 | 100.00 | 0.00 | — |

| | $AUC_{0-t}$ | $AUC_{0-\infty}$ | $C_{max}$ |
|---|---|---|---|
| Ratio of LS Means calculated using least squares means (ln-transformed data) | 94.09% | 93.69% | 110.73% |
| Ratio of Arithmetic Means calculated using arithmetic means (untransformed data) | 92.17% | 91.79% | 107.71% |
| 90% Geometric Confidence Interval using ln-transformed data | 89.15% to 99.31% | 89.09% to 98.53% | 101.84% to 120.39% |
| Intra-Subject CV | 10.27% | 9.58% | 15.98% |

An IDD-P™ fenofibrate formulation prepared by a hot melt microfluidization process described herein under GMP conditions according to the method of Example 15 was dried by lyophilization and formulated into tablets containing 160 mg of fenofibrate. In the formulation, the IDD-P™ fenofibrate was in the form of microfluidized microparticles stabilized by phospholipid LIPOID E80 and was prepared by microfluidization in the presence of sucrose and sorbitol. The oral bioavailability of the tableted IDD-P™ fenofibrate formulation was tested in the fasting and fed states in a single dose pharmacokinetic study. The study consisted of the administration of a single IDD-P™ fenofibrate tablet containing 160 mg of fenofibrate in 8 human subjects using a crossover design with randomized sequences. The fed condition was obtained with a high fat meal containing 1000 Kcal and 50 g fat. The blood samples were collected before and after each administration at various time points over 96 hours. The drug concentration in blood samples was determined by high-pressure liquid chromatography by monitoring for the level of the metabolite, fenofibric acid. The bioavailability of the drug from a dosage form such as an orally administered composition of the drug is given by the accumulated amount of drug versus time detected in a patient, and is calculated as the area under the curve of a plot of fenofibric acid concentrations detected in blood versus time. The bioavailability ($AUC_{0-\infty 4}$) data obtained under the fed and fasted conditions are presented in Table 7. The food effect is represented by the ratio of the $AUC_{0-\infty}$ under fed and fasted conditions. The ratio of 95% (fasted/fed) demonstrates the essential absence of food effect on the bioavailability of IDD-P™ fenofibrate. The ratio of the $AUC_{0-\infty}$ under fasted/fed conditions is 1.07. Thus the bioavailability of microfluidized phospholipid stabilized microparticles of fenofibrate increases by less than 8% between fasted and fed conditions in this example.

TABLE 7

$AUC_{0-\infty}$ for fenofibric acid under fasted and fed conditions

| | $AUC_{0-\infty}$ (ng.ml$^{-1}$.h) |
|---|---|
| Fasting state | 126282 |
| Fed state | 135201 |
| $F_{rel}$ (fasted/fed)$^{(1)}$ | 0.95 |

$^{(1)}$Ratio of the least-squares means using ln-transformed data

EXAMPLE 21

The following formulations were prepared according to the method of example 10 leading to a suspension before drying:
21-1) 10% fenofibrate, 3% LIPOID E80, 10% sucrose;
10% fenofibrate, 3% LIPOID E80, 10% sucrose, 5% sorbitol;
10% fenofibrate, 3% LIPOID E80, 10% sucrose, 1% sorbitol;
9% fenofibrate, 2.7% LIPOID E80, 19% sucrose, 4.5% sorbitol.

The formulations were spray dried in a commercially available spray dryer consisting of a chamber with inside diameter of 1.22 meters and a cylindrical height of 1.14 meters with a 60° conical bottom. Electrically heated air was used as the process gas admitted via a ceiling disperser. Each spray dried formulation was isolated initially as a dried powder that could be handled in a dry atmosphere without caking. A sample of spray dried powder prepared from formulation 21-2 that had an initial volume weighted average particle size of 1.7 microns in suspension before spray drying was reconstituted with mild sonication in simulated gastric fluid comprised of 2 g NaCl and 7 ml of conc. HCl per liter and found to have an average particle size of 1.9 microns.

EXAMPLE 22

A mixture of LIPOID E80 and fenofibrate was homogeneously dispersed in 10 mM pH 8.0+/−0.2 aqueous phosphate buffer using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension was then batchwise homogenized in 3 to 10 batch volume cycles using a Microfluidizer M110Y operated at 3,400 to 3,600 psig while maintained at 85° C. to 99° C. to form a heated homogenate containing the drug. The heated homogenate was cooled by passage through a heat exchanger cooled by chilled water at 5° C. to 10° C. and the transiently stable cooled homogenate was further homogenized for 10 to 20 batch volume cycles using a Microfluidics M110 EH homogenizer operated at 18,000 psig (peak) while maintained below 13° C. The resulting cooled dispersion comprising small particles containing fenofibrate stabilized with phospholipid was then treated with bulking agents and excipients, mixed at ambient temperature, and then dried by spray drying. The following compositions (in wt %) were prepared by this method as powders having volume weighted diameter after reconstitution with mild sonication of 1 to 2 microns with smallest mode (vol. wt) unsonicated as 1.5 microns. The powders produced were easily flowing, easily transferable by pouring, and exhibited no sticking. Water content in these powders was found to be less than 2.5%, and in some cases such as 22-e, about 1%.

| Suspension No. | Fenofibrate | Lipoid E80 | Sucrose | Mannitol | Ac-Di-Sol | Cab-O-Sil (colloidal silica) |
| --- | --- | --- | --- | --- | --- | --- |
| 22-a | 10.0 | 0.5 | 17.5 | | | |
| 22-b | 10.0 | 0.5 | 17.5 | | 1.8 | |
| 22-c | 10.0 | 0.5 | 17.5 | | | 0.5 |
| 22-d | 10.0 | 0.5 | 7 | | 3 | 0.5 |
| 22-e | 10.0 | 0.5 | | 7 | 3 | 0.5 |
| 22-f | 10.0 | 0.5 | 17.5 | | 1.8 | 0.5 |

Spray dried powders (100 parts) were blended with excipients AVICEL®PH102 (18.5 parts), AC-DI-SOL® (3.95 parts), CAB-O-SIL®(0.62 parts), and magnesium stearate (0.25 parts), processed into 1 mm granules or slugs by preliminary compression of the blend followed by crushing and seiving (USP Standard #14 sieve), blended with additional magnesium sterarate, and then compressed into tablet dosage forms. Hardness of the tablets produced in different batches ranged from 2 to 9 KPa either in an automatic tableting machine or by manual compression using a CMS-15 tablet press (Cadmach Machinaries). Disintegration times of these tablets were in the range of 3 to 10 minutes.

EXAMPLE 23

A two-treatment, two-period, two-sequence crossover clinical study was performed to evaluate the relative bioavailability of fenofibric acid in blood in 24 healthy volunteers after single dose oral administration of a tablet formulation of this invention comprising phospholipid stabilized microparticles of fenofibrate. The fenofibrate tablet dosage form consisted of 160 mg of fenofibrate and was derived from a dried lyophilized powder of this invention that contained between 0.1% and 3% moisture, and that was obtained from a suspension of microparticles consisting of 10% fenofibrate, 3% LIPOID E80, 10% sucrose, and 5% sorbitol, and that was further blended with sucrose at 5% by weight of the powder plus magnesium stearate at 0.2% plus colloidal silica at 0.2%. The bioavailability of fenofibric acid from the formulation of this invention was compared relative to that of commercially available micronized fenofibrate (TRICOR™) in a 200 mg capsule. Each dosage form was taken orally within 5 minutes after a low-fat test meal. The study was divided into 2 study periods, study period 1 and study period 2. At each period a single fenofibrate dose was administered to the subjects. There was a washout period of 10 days between the 2 administrations. Plasma samples were collected before each administration and during the 96 hours following each administration. Assay of fenofibric acid was performed with a validated analytical method (HPLC-UV) on the plasma samples. Relevant pharmacokinetic parameters were determined to evaluate the bioavailability of fenofibric acid after administration of each formulation, and the test formulation was compared to the reference formulation. The following results demonstrate bioequivalence between the formulation of this invention and the commercially available micronized fenofibrate (TRICOR) under low fat fed conditions.

What is claimed is:

1. A process for the preparation of small particles containing a poorly water soluble drug comprising:
   (a) mixing at high shear an admixture of a poorly water soluble drug and one or more than one surface active substance in an aqueous carrier in the absence of an organic solvent within a first temperature range at or above the melting point of the poorly water soluble drug to form a heated suspension containing the drug wherein the drug is molten;
   (b) homogenizing said heated suspension in a first pressure range and within said first temperature range to form a heated homogenate containing the drug wherein the drug is molten;
   (c) cooling said heated homogenate to a second temperature range below the melting temperature of the poorly water soluble drug to form a transiently stable cooled homogenate containing the drug;
   (d) applying a particle stabilizing energetic process comprising microfluidization, sonication, or milling to said cooled homogenate within a second temperature range below the melting point of the drug and in a second pressure range to form a cooled dispersion of stabilized small particles containing the drug; and
   (e) drying said cooled dispersion to form dried small particles containing the poorly water soluble drug.

2. The process of claim 1 wherein the admixture further comprises a bulking agent.

3. The process of claim 1 wherein the heated suspension further comprises a bulking agent.

4. The process of claim 1 wherein the heated homogenate further comprises a bulking agent.

5. The process of claim 1 wherein the cooled homogenate further comprises a bulking agent.

6. The process of claim 1 wherein the cooled dispersion further comprises a bulking agent.

7. The process of claim 2, wherein the bulking agent is selected from the group consisting of a monosaccharide, a disaccharide, a trisaccharide, sucrose, lactose, mannitol, sorbitol, trehalose, glycerol, dextrose, fructose, a sugar, a pentose, a hexose, xylitol, and mixtures thereof.

8. The process of claim 7 wherein the bulking agent is selected from the group consisting of trehalose, sucrose, sorbitol and mixtures thereof.

9. The process of claim 8 wherein the bulking agent is trehalose.

10. The process of claim 8 wherein the bulking agent is a mixture of sucrose and sorbitol.

11. The process of claim 1 wherein the surface active substance is a phospholipid substance.

12. The process of claim 1 wherein the surface active substance is selected from the group consisting of egg lecithin, egg phosphatidylcholine, soy phosphatidylcholine, dimyristoyl phosphatidylglycerol, a hydrogenated soy lecithin, and mixtures thereof.

13. The process of claim 1 wherein the first temperature range is from the melting point of the drug to 20° C. higher than the melting point of the drug.

14. The process of claim 1 wherein the second temperature range is from 4° C. to 20° C. and wherein the poorly water soluble drug is not molten.

15. The process of claim 1 wherein the aqueous carrier is selected from the group consisting of water, sterile water, water for injection, and phosphate buffered water having a pH from 4 to 10.

16. The process of claim 1 wherein the aqueous carrier is phosphate buffered water having a pH from 7 to 9.

17. The process of claim 1 wherein the aqueous carrier is phosphate buffered water having a pH from 7.5 to 8.5.

18. The process of claim 1 wherein the first pressure range is from 2,000 to 30,000 psi.

19. The process of claim 1 wherein the second pressure range is 18,000 to 5,000 psi.

20. The process of claim 1 wherein the small particles containing the drug have an average size in the range from 0.1 to 2 micrometers.

21. The process of claim 1 wherein the small particles containing the drug have an average size in the range from 0.3 to 2 micrometers.

22. A process for the preparation of small particles containing fenofibrate comprising:
    (a) mixing at high shear an admixture of fenofibrate and a phospholipid substance in an aqueous carrier in the absence of an organic solvent within a first temperature range at or above the melting point of fenofibrate to form a heated suspension wherein fenofibrate is molten;
    (b) homogenizing said heated suspension in a first pressure range and within said first temperature range to form a heated homogenate containing fenofibrate;
    (c) cooling said heated homogenate to a second temperature range below the melting temperature of fenofibrate to form a transiently stable cooled homogenate containing fenofibrate;
    (d) applying a particle stabilizing energetic process comprising microfluidization, sonication or milling to said cooled homogenate within a second temperature range below the melting temperature of fenofibrate and in a second pressure range to form a cooled dispersion of small particles containing fenofibrate, and
    (e) drying said cooled dispersion to form dried small particles containing fenofibrate.

23. The process of claim 22 wherein the admixture further comprises a bulking agent.

24. The process of claim 22 wherein the heated suspension further comprises a bulking agent.

25. The process of claim 22 wherein the heated homogenate further comprises a bulking agent.

26. The process of claim 22 wherein the cooled homogenate further comprises a bulking agent.

27. The process of claim 22 wherein the cooled dispersion further comprises a bulking agent.

28. The process of claim 22, wherein the bulking agent is selected from the group consisting of a monosaccharide, a disaccharide, a trisaccharide, sucrose, lactose, mannitol, sorbitol, trehalose, glycerol, dextrose, fructose, a sugar, a pentose, a hexose, xylitol, and mixtures thereof.

29. The process of claim 22 wherein the bulking agent is selected from the group consisting of trehalose, sucrose, sorbitol and mixtures thereof.

30. The process of claim 22 wherein the bulking agent is trehalose.

31. The process of claim 29 wherein the bulking agent is a mixture of sucrose and sorbitol.

32. The process of claim 22 wherein the surface active substance is selected from the group consisting of egg lecithin, egg phosphatidylcholine, soy phosphatidylcholine, dimyristoyl phosphatidylglycerol, a hydrogenated soy lecithin, and mixtures thereof.

33. The process of claim 22 wherein the first temperature range is at or above the melting point of fenofibrate.

34. The process of claim 22 wherein the first temperature range is from the melting point of fenofibrate to 20° C. above the melting point of fenofibrate.

35. The process of claim 22 wherein the second temperature range is below the melting point of fenofibrate.

36. The process of claim 35 wherein the second temperature range is from 4° C. to 40° C. and fenofibrate is not molten.

37. The process of claim 22 wherein the aqueous carrier is selected from the group consisting of water, sterile water, water for injection, and phosphate buffered water having a pH from 4 to 10.

38. The process of claim 22 wherein the aqueous carrier is phosphate buffered water having a pH from 7 to 9.

39. The process of claim 22 wherein the aqueous carrier is phosphate buffered water having a pH from 7.5 to 8.5.

40. The process of claim 22 wherein the first pressure range is from 2,000 to 30,000 psi.

41. The process of claim 22 wherein the second pressure range is 18,000 to 5,000 psi.

42. The process of claim 22 wherein the small particles have size in the range from 0.05 to 2 micrometers.

43. The process of claim 1 wherein the drug has a melting point between 37° C. and 275° C.

44. The process of claim 1 wherein the drug has a melting point between 50° C. up to but not including 100° C.

45. The process of claim 1 wherein the drug has a melting point between 100° C. up to 275° C.

46. The process of claim 1 wherein the drug is selected from the group consisting of camptothecin, nitrocamptothecin, 9-nitrocamptothecin, propranolol, and lovastatin.

47. The process of claim 1 where the cooled dispersion is dried by spray drying or by lyophilization.

48. The process of claim 22 wherein the cooled dispersion is dried by spray drying or by lyophilization.

49. The process of claim 1 wherein particle stabilizing energetic process comprises microfluidization or sonication.

50. The process of claim 49 wherein the particle stabilizing energetic process comprises microfluidization.

51. The process of claim 1 wherein the particle stabilizing energetic process further comprises high shear mixing.

52. The process of claim 1 wherein the surface active substance is an animal phospholipid, a plant phospholipid, an egg phospholipid, and combinations thereof.

53. The process of claim 1 wherein the surface active substance is a natural phospholipid, a synthetic or semi-synthetic phospholipid, in fully hydrogenated, partly hydrogenated or unsaturated form, in salted or desalted form, and combinations thereof.

54. The process of claim 1 wherein the poorly water soluble drug comprises fenofibrate.

* * * * *